(12) United States Patent
Diederichsen et al.

(10) Patent No.: US 7,893,325 B2
(45) Date of Patent: Feb. 22, 2011

(54) BRASSICA PLANT RESISTANT TO THE FUNGUS LEPTOSPHAERIA MACULANS (BLACKLEG)

(75) Inventors: Elke Diederichsen, Berlin (DE); Benjamin Laga, Gavere (BE); Johan Botterman, De Pinte (BE)

(73) Assignee: Bayer BioScience N.V. (BE)

( * ) Notice: Subject to any disclaimer, the term of this patent is extended or adjusted under 35 U.S.C. 154(b) by 778 days.

(21) Appl. No.: 11/023,034

(22) Filed: Dec. 23, 2004

(65) Prior Publication Data

US 2005/0142122 A1 Jun. 30, 2005

(30) Foreign Application Priority Data

Dec. 24, 2003 (AU) ............................ 2003271381

(51) Int. Cl.
*A01H 5/00* (2006.01)
*A01H 5/10* (2006.01)

(52) U.S. Cl. ................. 800/306; 800/300; 800/301; 800/303

(58) Field of Classification Search ............... 800/300, 800/301, 303, 306
See application file for complete search history.

(56) References Cited

U.S. PATENT DOCUMENTS

2002/0138881 A1* 9/2002 Charne et al. ............ 800/306

OTHER PUBLICATIONS

Snowdon et al. 2002. Theor Appl Genet 104: 533-538.*
Mithen et al. 1992. Plant Breeding 108: 60-68.*

F. Yu et al., "Identification of two loci in *Brassica napus* for resistance to *Leptosphaeria maculans*," *Can. J. Plant Pathol.*, 2002, vol. 24, pp. 96-97. (XP008045443).
R.F. Mithen et al., "Glucosinolates and Resistance to *Leptosphaeria maculans* in Wild and Cultivated Brassica Species," *Plant Breeding*, (1992), vol. 108, pp. 60-68. (XP008045453).
D.L. Woods et al., "CB 9940 and CB 9941 summer turnip rapes," *Can. J. Plant Sci.* (Mar. 2001), vol. 81, pp. 461-463. (XP008045485).
J. Siemens, "Interspecific Hybridisation between Wild Relatives and *Brassica napus* to Introduce New Resistance Traits into the Oilseed Rape Gene Pool," *Czech J. Genet. Plant Breed*, 2002, vol. 38 (3-4), pp. 155-157.
S.R. Rimmer et al., "Mapping resistance genes to *Leptosphaeria maculans* in *Brassica napus*," *Thirteenth Crucifer Genetics Workshop*, Mar. 23-26, 2002, University of California, Davis. (XP008045484).
I. Falak et al., "Development of Blackleg Resistant Canola Quality—B. Rapa," Prioneer Hi-Bred Production Ltd., 12111 Mississauga Rd., R.R. #4, Georgetown, Ontario, L7G 4S7, Canada. 1999.
T. Rouxel et al., "Abiotic elicitation of indole phytoalexins and resistance to *Leptosphaeria maculans* within *Brassiceae*," *Planta* (1991), vol. 184, pp. 271-278.

* cited by examiner

*Primary Examiner*—Medina Ibrahim
*Assistant Examiner*—Keith O. Robinson
(74) *Attorney, Agent, or Firm*—Connolly Bove Lodge & Hutz LLP

(57) ABSTRACT

The invention relates to fungal disease resistance, in particular to resistance to blackleg disease caused by *Leptosphaeria maculans*. Provided are *Brassica* plants and seeds comprising a fragment of chromosome 8 of a wild *B. rapa* accession in their genome, wherein this fragment comprises a blackleg resistance locus. Further provided are molecular markers linked to the blackleg resistance locus and methods of using the markers. *Brassica* plants and seeds with stacked blackleg resistance loci are also provided.

21 Claims, 1 Drawing Sheet

SEQUENCE LISTING

```
<160> NUMBER OF SEQ ID NOS: 20

<210> SEQ ID NO 1
<211> LENGTH: 16
<212> TYPE: DNA
<213> ORGANISM: artificial
<220> FEATURE:
<223> OTHER INFORMATION: MseI-adapter sequence 5'-3'

<400> SEQUENCE: 1
gacgatgagt cctgag                                                      16

<210> SEQ ID NO 2
<211> LENGTH: 14
<212> TYPE: DNA
<213> ORGANISM: artificial
<220> FEATURE:
<223> OTHER INFORMATION: MseI-adapter sequence 3'-5'

<400> SEQUENCE: 2
tactcaggac tcat                                                        14

<210> SEQ ID NO 3
<211> LENGTH: 17
<212> TYPE: DNA
<213> ORGANISM: artificial
<220> FEATURE:
<223> OTHER INFORMATION: EcoRI-adapter sequence 5'-3'

<400> SEQUENCE: 3
ctcgtagact gcgtacc                                                     17

<210> SEQ ID NO 4
<211> LENGTH: 15
<212> TYPE: DNA
<213> ORGANISM: artificial
<220> FEATURE:
<223> OTHER INFORMATION: EcoRI-adapter sequence 3'-5'

<400> SEQUENCE: 4
ctgacgcatg gttaa                                                       15

<210> SEQ ID NO 5
<211> LENGTH: 21
<212> TYPE: DNA
<213> ORGANISM: artificial
<220> FEATURE:
<223> OTHER INFORMATION: PstI-adapter sequence 5'-3'

<400> SEQUENCE: 5
ctcgtagact gcgtacatgc a                                                21

<210> SEQ ID NO 6
<211> LENGTH: 14
```

```
<212> TYPE: DNA
<213> ORGANISM: artificial
<220> FEATURE:
<223> OTHER INFORMATION: PstI-adapter sequence 3'-5'

<400> SEQUENCE: 6
catctgacgc atgt                                                        14

<210> SEQ ID NO 7
<211> LENGTH: 17
<212> TYPE: DNA
<213> ORGANISM: artificial
<220> FEATURE:
<223> OTHER INFORMATION: AFLP primer E01

<400> SEQUENCE: 7
gactgcgtac caattca                                                     17

<210> SEQ ID NO 8
<211> LENGTH: 17
<212> TYPE: DNA
<213> ORGANISM: artificial
<220> FEATURE:
<223> OTHER INFORMATION: AFLP primer M01

<400> SEQUENCE: 8
gatgagtcct gagtaaa                                                     17

<210> SEQ ID NO 9
<211> LENGTH: 17
<212> TYPE: DNA
<213> ORGANISM: artificial
<220> FEATURE:
<223> OTHER INFORMATION: AFLP primer M02

<400> SEQUENCE: 9
gatgagtcct gagtaac                                                     17

<210> SEQ ID NO 10
<211> LENGTH: 17
<212> TYPE: DNA
<213> ORGANISM: artificial
<220> FEATURE:
<223> OTHER INFORMATION: AFLP primer P01

<400> SEQUENCE: 10
gactgcgtac atgcaga                                                     17

<210> SEQ ID NO 11
<211> LENGTH: 19
<212> TYPE: DNA
<213> ORGANISM: artificial
<220> FEATURE:
<223> OTHER INFORMATION: AFLP primer E31

<400> SEQUENCE: 11
gactgcgtac caattcaaa                                                   19

<210> SEQ ID NO 12
<211> LENGTH: 19
<212> TYPE: DNA
<213> ORGANISM: artificial
<220> FEATURE:
<223> OTHER INFORMATION: AFLP primer E32

<400> SEQUENCE: 12
```

-continued gactgcgtac caattcaac                                                19

<210> SEQ ID NO 13
<211> LENGTH: 19
<212> TYPE: DNA
<213> ORGANISM: artificial
<220> FEATURE:
<223> OTHER INFORMATION: AFLP primer E36

<400> SEQUENCE: 13
gactgcgtac caattcacc                                                19

<210> SEQ ID NO 14
<211> LENGTH: 19
<212> TYPE: DNA
<213> ORGANISM: artificial
<220> FEATURE:
<223> OTHER INFORMATION: AFLP primer M48

<400> SEQUENCE: 14
gatgagtcct gagtaacac                                                19

<210> SEQ ID NO 15
<211> LENGTH: 19
<212> TYPE: DNA
<213> ORGANISM: artificial
<220> FEATURE:
<223> OTHER INFORMATION: AFLP primer M50

<400> SEQUENCE: 15
gatgagtcct gagtaacat                                                19

<210> SEQ ID NO 16
<211> LENGTH: 19
<212> TYPE: DNA
<213> ORGANISM: artificial
<220> FEATURE:
<223> OTHER INFORMATION: AFLP primer M51

<400> SEQUENCE: 16
gatgagtcct gagtaacca                                                19

<210> SEQ ID NO 17
<211> LENGTH: 19
<212> TYPE: DNA
<213> ORGANISM: artificial
<220> FEATURE:
<223> OTHER INFORMATION: AFLP primer M59

<400> SEQUENCE: 17
gatgagtcct gagtaacta                                                19

<210> SEQ ID NO 18
<211> LENGTH: 19
<212> TYPE: DNA
<213> ORGANISM: artificial
<220> FEATURE:
<223> OTHER INFORMATION: AFLP primer M61

<400> SEQUENCE: 18
gatgagtcct gagtaactg                                                19

<210> SEQ ID NO 19
<211> LENGTH: 19
<212> TYPE: DNA
<213> ORGANISM: artificial

```
<220> FEATURE:
<223> OTHER INFORMATION: AFLP primer P31

<400> SEQUENCE: 19
gactgcgtac atgcagaaa                                                    19

<210> SEQ ID NO 20
<211> LENGTH: 19
<212> TYPE: DNA
<213> ORGANISM: artificial
<220> FEATURE:
<223> OTHER INFORMATION: AFLP primer P34

<400> SEQUENCE: 20
gactgcgtac atgcagaat                                                    19
```

BRASSICA PLANT RESISTANT TO THE FUNGUS LEPTOSPHAERIA MACULANS (BLACKLEG)

This application claims the benefit of foreign priority of Australian patent application number 2003271381 filed Dec. 24, 2003, which is incorporated by reference herein.

FIELD OF THE INVENTION

The invention relates to the field of fungal disease control in *Brassica napus*. Provided are *B. napus* plants and seeds comprising a blackleg resistance locus, derived from *B. rapa* chromosome 8, in their genome. Also provided are *B. napus* plants and seeds comprising at least two or at least three blackleg resistance loci, located on different chromosomes, in their genome. Further provided are detection tools for detecting the presence of one or more resistance alleles in *B. napus* plants, tissue or seeds, as well as methods for transferring one or more resistance loci to other *Brassica* plants and methods for combining different resistance loci in hybrid seeds and plants. Methods for enhancing durability of resistance to *L. maculans* are also provided, as well as uses of the plants and seeds and the processes or kits of the invention.

BACKGROUND ART

Blackleg or stem canker is a major disease of *Brassica napus* L. (oilseed rape or Canola), causing annually major economic losses worldwide, in particular in Europe, Australia and North America. Blackleg is caused by the fungal pathogen *Leptosphaeria maculans* (Desm.) Ces. & De Not. (anamorph *Phoma lingam* Tode ex. Fr.). *L. maculans* symptoms can develop on cotyledons, leaves, pods and stems. Leaf lesions develop after infection by wind dispersed ascospores and/or water (splash) dispersed conidiospores. Stem symptoms (or cankers) can arise through direct infection of the stems or through systemic growth of the fungus from leaf lesions, through the vascular tissue into the stem [Hammond et al. (1985), *Plant Pathology* 34: 557-565]. Stem cankers may girdle the stem, which can lead to the lodging of plants and plant death. Less severe cankers can cause a restriction in water and nutrient flow, which in turn may lead to shriveling of seeds and pods. Pod infection can lead to premature pod-shatter and seed infection.

The incorporation of blackleg resistance into *B. napus* cultivars is one of the major objectives in breeding programs worldwide. Although both the spraying of fungicides and cultural practices are used to reduce yield losses caused by blackleg infection, the most reliable method of control to date is genetic resistance. *Brassica napus* (2n=38, genome AACC) is an amphidiploid species, which originated from a spontaneous hybridization of *Brassica rapa* L. (syn. *B. campestris*; 2n=20, AA) and *Brassica oleracea* L. (2n=18, CC). *B. napus* contains the complete chromosome sets of these two diploid genomes.

Blackleg resistance is assessed either in glasshouse or in field experiments, in one embodiment blackleg resistance is preferably assessed in field experiments, and can be assessed at different stages of the plant development. When referring to blackleg resistance, normally different types of resistance are therefore distinguished depending on the plant stage and tissue assessed, such as seedling resistance ('early' resistance) and adult plant resistance ('late' or 'stem' resistance). Plant tissues analyzed for resistance are for example cotyledons, leaves and stem bases. Genetical resistance to blackleg has been reported to be either monogenic (under control of a major gene) or polygenic (under control of several minor genes).

A number of resistance loci have been mapped in *B. napus*. For example, a single dominant resistance locus, designated LEM1, was reported to be located on linkage group 6 (which is now known to the inventors to be chromosome N07 in the nomenclature of Sharpe et al. (1995, *Genome* 38: 1112-1121)) of *B. napus* cv. Major, based on wound inoculations of seedlings [Fereirra et al. (1995), *Genetics* 85 (2): 213-217]. Field resistance in adult plants, in spring cv. Cresor, was mapped to chromosome N07 by Dion et al. [(1995), *TAG* 91: 1190-1194] and designated LmFr. Cultivars Maluka and Shiralee were reported to have a major locus controlling seedling resistance, designated LmR1, on chromosome N07 [Mayerhofer et al. (1997), *Genome* 40: 294-301.]. Rimmer et al. [(1999), *Proceedings of the 10th International Rapeseed Congress*] also reported resistance loci, designated RLM, on chromosome N07.

However, the lack of adequate resistance found in *Brassica napus* (AACC genome) and the continuous threat of breakdown of resistance when a resistant cultivar is used widespread and over longer time periods, has lead breeders and scientists to search for alternative sources of resistance. The main focus has been on the identification and transfer of resistance alleles from related *Brassica* species, such as *B. rapa* (AA), *B. oleracea* (CC), *B. nigra* (BB genome), *B. juncea* (AABB genome) and *B. carinata* (BBCC).

One major source of blackleg resistance is the B genome. Gerdemann-Knörck reported in 1994 the introduction of blackleg resistance into *B. napus* from *B. nigra* by asymmetric somatic hybridization [Gerdemann-Knörck et al. (1994), *Plant Breeding* 113: 106-113].

Another approach has been to generate so-called 'synthetic' *B. napus* lines by interspecific hybridization of two diploid species (AA and CC genome) and subsequent in vitro culture of embryos and chromosome doubling.

Blackleg resistance was introduced into *B. napus* in this way by generating synthetic *B. napus* plants from wild *B. rapa* (AA genome) accessions [Crouch et al. (1994), Plant Breeding 112: 265-278] and wild *B. atlantica* (CC genome) accessions [Mithen and Magrath (1992), *Plant Breeding* 108: 60-68, and Mithen and Herron (1991), *Proceedings of the 8th International Rapeseed Congress*].

Six accessions of wild *B. rapa* ssp *sylvestris* were crossed with *B. oleracea* ssp *alboglabra* in order to develop a series of synthetic *B. napus* lines with a common C genome but different A genomes [Crouch et al. (1994), supra]. *B. rapa* ssp *sylvestris* #75 and #76 were found to be resistant to blackleg isolates in glasshouse tests (cotyledon and leaf tests), while *B. rapa* ssp *sylvestris* #29 was susceptible. Two of the synthetic lines derived from #75 or #76 and *B. oleracea* ssp *alboglabra*, and their F1 hybrids with oilseed rape cultivars, showed high resistance to blackleg in glasshouse experiments. Only one of these lines also showed resistance in field experiments in England and Australia.

Crouch (PhD thesis, University of East Anglia, Norwich, UK) describes RFLP markers linked to regions of the genome contributing to field resistance, the mapping of these regions to five linkage groups and the localization of quantitative trait loci (QTL) contributing to resistance in different tissues. Interval analysis identified QTL contributing to leaf resistance in both Group 1 from the synthetic parent [chromosome N7 according to Sharpe et al. (1995), *Genome* 38: 1112-1121] and Group 3 from the cultivar parent (chromosome N3 according to Sharpe et al.) and QTL contributing to resistance in the lower part of the stem, hypocotyl and root on Group 1, Group 2 (chromosome N10 according to Sharpe et al.) and Group 5 (the association of this group with the linkage groups of Sharpe et al., is uncertain). Interval mapping failed to identify any QTL contributing to resistance in the upper part of the stem.

The synthetic *B. napus* lines described by Crouch and Mithen (supra) were agronomically not suitable, as they contained high glucosinolate levels, high erucic acid levels, had poor fertility and suffered from self-incompatibility [Easton, *Australian Research Assembly on Brassicas* (2001)].

In spring 2000 Pacific Seeds brought the open-pollinated *B. napus* variety Surpass400 onto the market in Australia, which received a national blackleg resistance rating of 9.0, the highest known level of resistance. The ancestry of Surpass400 includes a 'synthetic' *B. napus*, derived from inter-specific crosses between wild *B. rapa* ssp *sylvestris* from Sicily and *B. oleracea* ssp *alboglabra* [Li et al., *Australian Research Assembly on Brassicas* 2001; Easton, supra]. A major dominant allele for blackleg resistance at the seedling stage was reported to be present in Surpass400 [Li et al., *Australian Research Assembly on Brassicas* 2001].

Yu et al. [(2002), *Can. J. Plant Pathology* 24: 96-97; Plant, Animal & Microbe Genomes Conference Jan. 12-16, (2002)] reported two resistance loci in *B. napus* populations derived from crosses with breeding lines 6270 and 6279. The dominant nuclear allele designated LepR1 on chromosome $NO_2$ conferred resistance in line 6270 to *L. maculans* isolates from pathogenicity groups PG2, PG3 and PG4. The second locus, designated LepR2 located on chromosome N10, was incompletely dominant and conferred cotyledon resistance to PG2 and PG3 isolates.

Rimmer et al. [$13^{th}$ *Crucifer Genetics Workshop*, Mar. 23-26, (2002)] reported the mapping of four resistance loci in *B. napus*. Two resistance loci were derived from *B. napus* (not from *B. rapa*) and mapped to chromosome N7 and chromosome N8. The other two loci were derived from *B. rapa* ssp *sylvestris* and mapped to chromosome 2 and chromosome 10.

Early 2003 the first reports of a breakdown of Surpass400 resistance were made. A more virulent strain of the fungus seems to have evolved in just three years, able to infect Surpass400. How quickly this strain will be able to spread to different locations remains to be seen, but new resistance genes and methods of enhancing durability of resistance are clearly needed.

With the constant threat of genetic resistance breaking down as a result of changes in the pathogen population, it is desirable to identify new genetic sources of resistance, methods for transferring these into varieties with high agronomic performance and methods for enhancing durability of resistance. The present invention, including the different embodiments provided in the specifications and claims, provides plants comprising a novel blackleg resistance gene, Lem-08-syl and methods and means for transferring Lem-08-syl into other breeding lines or varieties, as well as methods of detecting the presence/absence of Lem-08-syl in plants.

SUMMARY OF THE INVENTION

In one embodiment of this invention *B. juncea* plants, seeds and tissues comprising a new blackleg resistance gene on chromosome 8, are provided, wherein the resistance gene is derived from *B. rapa*. In another embodiment of the invention, *B. juncea* plants are provided comprising a fragment of *B. rapa* chromosome R08, wherein said fragment comprises a blackleg resistance gene. The *B. rapa* plants in the preceding sentences can be from wild *B. rapa* accessions such as *B. rapa* ssp *sylvestris*, *B. rapa* ssp *chinensis*, *B. rapa* ssp *dichotoma*, *B. rapa* ssp *japonica*, *B. rapa* ssp *narinosa*, *B. rapa* ssp *olifeira*, *B. rapa* ssp *pekinensis*, *B. rapa* ssp *perviridis*, *B. rapa* ssp *trilocul*.

In an embodiment of this invention, *B. napus* plants are provided comprising a fragment of *B. rapa* chromosome R08, wherein said fragment comprises a blackleg resistance gene, wherein these *B. napus* plants are selected from the group consisting of: a *B. napus* plant containing a transgene integrated into its genome, progeny of a *B. napus* plant containing said blackleg resistance gene, wherein said progeny results from crosses between *B. napus* plants containing said blackleg resistance gene and Surpass400 plants, a *B. napus* plant that contains a level of aliphatic glucosinolates in dry, defatted seed meal of less than 30 mmol/g, a *B. napus* plant the solid component of the seed contains less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid; a *B. napus* plant that produces an oil (after crushing the seeds) containing less than 2% erucic acid (of the total fatty acids in the oil); a *B. napus* spring oilseed rape plant, a *B. napus* winter oilseed rape plant, a *B. napus* plant that does not contain a blackleg resistance gene on chromosome N2, a *B. napus* plant that does not contain a blackleg resistance gene on chromosome N10; a *B. napus* plants that does not contain a resistance gene mapped on chromosome 2 or a resistance gene mapped on chromosome 10, which resistance gene is derived from *B. rapa* ssp. *Sylvestris*; a *B. napus* plant comprising a transgene that can render plants male sterile, preferably a barnase gene; progeny of a *B. napus* plant containing said blackleg resistance gene, wherein said progeny results from crosses between *B. napus* plants containing said blackleg resistance gene and any one of the following oilseed rape varieties: a herbicide resistant *B. napus* variety, a *B. napus* variety with high oil content in its seeds, a *B. napus* variety with high oleic acid content in its seeds, a *B. napus* variety with low linolenic acid content in its seeds, Jet Neuf, Quantum, Maluka, Hyola43, Hyola60, Surpass400, Surpass402CL, Surpass603CL, Surpass501TT, a RoundupReady™ plant, a LibertyLink™ plant, a plant comprising a male sterility transgene, InVigor® 40, InVigor® 70, InVigor® 90, InVigor® 2573, InVigor® 2663, InVigor® 2733, InVigor® 5020, InVigor® 5030, or InVigor® 5070.

In a further embodiment of this invention the *B. napus* plants, seeds and tissues described herein above comprise the new blackleg resistance gene on chromosome 8.

The *B. rapa* plants in the preceding paragraphs can be from wild *B. rapa* accessions such as *B. rapa* ssp *sylvestris*, *B. rapa* ssp *chinensis*, *B. rapa* ssp *dichotoma*, *B. rapa* ssp *japonica*, *B. rapa* ssp *narinosa*, *B. rapa* ssp *olifeira*, *B. rapa* ssp *pekinensis*, *B. rapa* ssp *perviridis*, *B. rapa* ssp *trilocul*.

In a further embodiment of this invention the blackleg resistance gene has been transferred to said *B. napus* or *B. juncea* plants by genetic transformation.

In still another embodiment of this invention, the above blackleg resistance gene comprises Lem-08-syl as defined herein, particularly when Lem-08-syl is associated with at least one AFLP marker selected from the group consisting of: P34/M48-M283.0, P31/M59-M97.1, E32/M48-M162.7, E31/M61-M237.6, E32/M50-M362.0, and E36/M51-M171.1.

In another embodiment of the invention, one or more molecular markers, such as AFLP markers, linked to the blackleg resistance gene from *B. rapa*, particularly from chromosome 8 of *B. rapa*, are provided. In one particular embodiment, the molecular markers to be used in this invention are selected from *B. rapa* specific markers, such as E32/M50-

M362.0, E36/M51-M171.1 or P34/M48-M283, or are selected from the markers P31/M59-M97.1, E32/M48-M162.7 or E31/M61-M237.6.

In a further embodiment hybrid seeds comprising a blackleg resistance gene from *B. rapa* chromosome R08 are provided, wherein such hybrid seeds develop plants which have the characteristics set out in the second full paragraph of this summary.

*B. napus* seeds deposited at the ATCC under accession number PTA-5410 are also provided, as well as methods of using these seeds to introgress the blackleg resistance gene located on chromosome R08 of *B. rapa* into other *Brassica* breeding lines or varieties, and *B. napus* or *B. juncea* plants derived from such seeds and comprising the blackleg resistance gene of this invention.

In a further embodiment of the invention *B. napus* or *B. juncea* plants or seeds comprising at least two, preferably at least three or four, blackleg resistance genes, each located on a different chromosome, are provided. This includes plants comprising a blackleg resistance gene on chromosome N08 and further comprising a blackleg resistance gene on chromosome N07, N10 and/or N14, or a blackleg resistance gene of *B. napus* cv. Jet Neuf, Quantum, Maluka, Hyola60, or Surpass400. In one embodiment plants comprising at least two *B. rapa* derived blackleg resistance loci, such as on chromosome N08 and on chromosome N10, are provided.

The invention further provides methods of hybrid seed production, whereby blackleg resistance loci are stacked in the hybrid seeds or plants. The methods comprise crossing a male sterile parent plant, preferably a plant comprising a barnase gene under the control of a tapetum- or stamen-specific promoter, comprising a blackleg resistance gene from *B. rapa* of this invention, with a plant comprising in its genome a gene for restoring fertility, preferably with one or more blackleg resistance loci on a chromosome other than chromosome 8, such as loci on chromosome N07, N10 and/or N14, or a resistance gene of Jet Neuf, Quantum, Maluka, Hyola60, or Surpass400. In another method, the male sterile parent comprises the blackleg resistance gene of this invention, and one or more additional blackleg resistance loci, such as a resistance locus on chromosome N07, N10 and/or N14, or a resistance gene of Jet Neuf, Quantum, Maluka, Hyola60, or Surpass400. This plant is crossed with a plant comprising a gene for restoring fertility.

In one embodiment hybrid plants and seeds comprising at least a blackleg resistance gene of *B. rapa* chromosome R08 are provided. In a further embodiment are provided hybrid plants and seeds comprising further blackleg resistance loci on other chromosomes, such as Lem10, Lem7, and/or Lem14. In one embodiment of this invention, progeny of crosses of the plants of this invention comprising the Lem-08-syl gene with plants of the known varieties Hyola 60, Hyola 43, Surpass501TT, Surpass400, Surpass404CL, Surpass402CL, Surpass603CL, or any other oilseed rape variety with a high blackleg resistance rating (see, e.g., Khangura et al., 2003, Department of Agriculture, Western Australia, Farmnote No. 6/2003, ISSN 0726-934x) are also provided.

Methods for transferring Lem-08-syl into other *Brassica* breeding lines or varieties are provided. In one embodiment marker assisted selection is used to accelerate transfer.

The invention also provides methods for detecting the presence or absence of Lem-08-syl in *Brassica* plants, seeds or tissues.

Detection kits, useful for detecting the presence or absence of Lem-08-syl in 5 *Brassica*, preferably *B. napus* or *B. juncea* plants, seeds or tissues are also provided. Also provided herein are any one of the AFLP markers of this invention, particularly any one of E32/M50-M362, E36/M51-M171.1, P34/M48-M283, P31/M59-M97.1, E32/M48-M162.7, and E31/M61-M237.6, preferably any one of AFLP markers E32/M50-M362, E36/M51-M171.1, and P34/M48-M283. One embodiment of this invention is directed to the use of such markers in AFLP analysis of *B. napus*, and a kit for *B. napus* analysis comprising such markers.

Also provided are the use of the plants or seeds of the invention in growing a crop of *Brassica* oilseed plants, preferably *B. napus* plants.

In another embodiment of this invention, the plants comprising a new blackleg resistance gene on chromosome 8, wherein the resistance gene is derived from *B. rapa*, as used herein, are *B. napus* plants that meet the canola quality standard set by the Canola Council of Canada (http://www.canola-council.org).

Some of the embodiments of the current invention are listed in the below numbered paragraphs:

1. A *B. juncea* plant comprising on chromosome 8 a fragment of a *B. rapa* chromosome, wherein said fragment comprises a blackleg resistance gene.
2. A *B. juncea* plant comprising a fragment of *B. rapa* chromosome R08, wherein said fragment comprises a blackleg resistance gene.
3. A *B. napus* plant comprising on chromosome 8 a fragment of a *B. rapa* chromosome, wherein said fragment comprises a blackleg resistance gene, and wherein said *B. napus* plant is selected from the group consisting of:
    a *B. napus* plant containing a transgene integrated into its genome,
    progeny of a *B. napus* plant containing said blackleg resistance gene, wherein said progeny results from crosses between *B. napus* plants containing said blackleg resistance gene and Surpass400 plants,
    a *B. napus* plant that contains a level of aliphatic glucosinolates in dry, defatted seed meal of less than 30 mmol/g,
    a *B. napus* plant the solid component of the seed contains less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid;
    a *B. napus* plant that produces an oil (after crushing the seeds) containing less than 2% erucic acid (of the total fatty acids in the oil);
    a *B. napus* spring oilseed rape plant,
    a *B. napus* winter oilseed rape plant,
    a *B. napus* plant that does not contain a blackleg resistance gene on chromosome N2,
    a *B. napus* plant that does not contain a blackleg resistance gene on chromosome N10;
    a *B. napus* plants that does not contain a resistance gene mapped on chromosome 2 or a resistance gene mapped on chromosome 10, which resistance gene is derived from *B. rapa* ssp. *Sylvestris*,
    a *B. napus* plant comprising a transgene that can render plants male sterile, preferably a barnase gene
    progeny of a *B. napus* plant containing said blackleg resistance gene, wherein said progeny results from crosses between *B. napus* plants containing said blackleg resistance gene any one of the following oilseed rape varieties: a herbicide resistant *B. napus* variety, a *B. napus* variety with high oil content in its seeds, a *B. napus* variety with high oleic acid content in its seeds, a *B. napus* variety with low linolenic acid content in its seeds, Jet Neuf, Quantum, Maluka, Hyola43, Hyola60, Surpass400, Surpass402CL, Surpass603CL, Surpass501TT, a RoundupReady™ plant, a LibertyLink™ plant, a plant comprising a male sterility transgene, InVigor® 40, InVigor® 70, InVigor® 90, InVigor® 2573, InVigor® 2663, InVigor® 2733, InVigor® 5020, InVigor® 5030, or InVigor® 5070.

4. A *B. napus* a plant comprising a fragment of *B. rapa* chromosome R08, wherein said fragment comprises a blackleg resistance gene, and wherein said *B. napus* plant is selected from the group consisting of:
   a *B. napus* plant containing a transgene integrated into its genome,
   progeny of a *B. napus* plant containing said blackleg resistance gene, wherein said progeny results from crosses between *B. napus* plants containing said blackleg resistance gene and Surpass400 plants,
   a *B. napus* plant that contains a level of aliphatic glucosinolates in dry, defatted seed meal of less than 30 mmol/g,
   a *B. napus* plant the solid component of the seed contains less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid;
   a *B. napus* plant that produces an oil (after crushing the seeds) containing less than 2% erucic acid (of the total fatty acids in the oil);
   a *B. napus* spring oilseed rape plant,
   a *B. napus* winter oilseed rape plant,
   a *B. napus* plant that does not contain a blackleg resistance gene on chromosome N2,
   a *B. napus* plant that does not contain a blackleg resistance gene on chromosome N10;
   a *B. napus* plants that does not contain a resistance gene mapped on chromosome 2 or a resistance gene mapped on chromosome 10, which resistance gene is derived from *B. rapa* ssp. *Sylvestris,*
   a *B. napus* plant comprising a transgene that can render plants male sterile, preferably a barnase gene;
   progeny of a *B. napus* plant containing said blackleg resistance gene, wherein said progeny results from crosses between *B. napus* plants containing said blackleg resistance gene any one of the following oilseed rape varieties: a herbicide resistant *B. napus* variety, a *B. napus* variety with high oil content in its seeds, a *B. napus* variety with high oleic acid content in its seeds, a *B. napus* variety with low linolenic acid content in its seeds, Jet Neuf, Quantum, Maluka, Hyola43, Hyola60, Surpass400, Surpass402CL, Surpass603CL, Surpass501TT, a RoundupReady™ plant, a LibertyLink™ plant, a plant comprising a male sterility transgene, InVigor® 40, InVigor® 70, InVigor® 90, InVigor® 2573, InVigor® 2663, InVigor® 2733, InVigor® 5020, InVigor® 5030, or InVigor® 5070.

5. The plant of any one of paragraphs 1 to 4, wherein said blackleg resistance gene has been transferred to said plant by genetic transformation.

6. The plant according to any one of paragraphs 1 to 5, wherein said *B. rapa* is *B. rapa* ssp. *sylvestris.*

7. The plant according to any one of paragraphs 1 to 6, wherein said resistance gene comprises Lem-08-syl.

8. The plant according to paragraph 7, wherein Lem-08-syl is associated with at least one AFLP marker selected from the group consisting of: P34/M48-M283.0, P31/M59-M97.1, E32/M48-M162.7, E31/M61-M237.6, E32/M50-M362.0, and E36/M51-M171.1.

9. The plant according to paragraph 8, wherein Lem-08-syl is associated with AFLP marker E32/M50-M362.0 or AFLP marker E36/M51-M171.1.

10. The plant according to paragraph 7, wherein Lem-08-syl is associated with at least one AFLP marker selected from the group consisting of: P34/M48-M283.0, P31/M59-M97.1, E32/M48-M162.7 and E31/M61-M237.6.

11. A *B. napus* plant derived from the seeds deposited at the ATCC under accession number PTA-5410.

12. The plant according to any one of paragraphs 1 to 11, further comprising in its genome at least one additional blackleg resistance gene located on a different chromosome.

13. The plant of paragraph 12, wherein said additional resistance gene is located on chromosome N10, N14 and/or N 7, or where said additional resistance gene is from any one of the following *B. napus* cultivars: Jet Neuf, Quantum, Maluka, Hyola60, or Surpass 400.

14. The plant according to paragraph 12 or 13, wherein said additional blackleg resistance locus is derived from *B. rapa.*

15. The plant according to any one of paragraphs 1 to 14, wherein said plant further comprises a barnase gene under control of a tapetum specific promoter in its genome.

16. Seeds of the plant according to any one of paragraphs 1 to 15, comprising said blackleg resistance gene.

17. Seeds according to paragraph 16, wherein said seeds are hybrid seeds.

18. Seeds deposited at the ATCC under accession number PTA-5410.

19. A method for producing hybrid *B. napus* seeds comprising several resistance loci in their genome, comprising:
    pollinating plants according to any one of paragraphs 1 to 15 which are male-sterile with pollen of *B. napus* plants comprising (a) a barstar gene under control of a tapetum specific promoter in its genome, and (b) a blackleg resistance gene on any one of chromosomes N10, N07 or N14, and
    harvesting the hybrid seeds from said male sterile plants.

20. A method for producing hybrid *B. napus* seeds, comprising:
    pollinating plants according to any one of paragraphs 1 to 15 which are male-sterile with pollen of *B. napus* plants comprising a barstar gene under control of a tapetum specific promoter in its genome, and
    harvesting the hybrid seeds from said male sterile plants.

21. Hybrid *B. napus* seeds, comprising a fragment of *B. rapa* chromosome R08, wherein said fragment comprises a blackleg resistance locus, wherein said hybrid *B. napus* seeds develop into plants, the solid component of the seeds contains less than 30 micromoles of any one or any mixture of 3-butenyl glucosinolate, 4-pentenyl glucosinolate, 3-hydroxy-3 butenyl glucosinolate, and 2-hydroxy-4-pentenyl glucosinolate per gram of air-dry, oil-free solid.

22. The hybrid seeds of paragraph 21, wherein said blackleg resistance gene is located on chromosome N08.

23. Plants derived from the hybrid seeds according to paragraph 21 or 22.

24. A method of enhancing durability of blackleg resistance, comprising combining at least two, preferably at least three, blackleg resistance loci in the genome of *B. napus* plants, whereby the resistance loci are Lem-08-syl and Lem-10-syl or Lem-07.

25. The method of paragraph 24, wherein said genome is the A genome.

26. A method for transferring the blackleg resistance gene according to paragraph 3 or 4 into another *B. napus* plant, comprising crossing the plant according to paragraph 3 or 4 with another *B. napus* plant, collecting F1 hybrid seeds from said cross, selfing or crossing the F1 plants derived from said F1 seeds for one or more generations and screening plants derived from said selfing or crossing for the presence of said chromosome fragment of *B. rapa* and selecting plants comprising said fragment.

27. The method according to paragraph 26, wherein said screening is done using molecular markers linked to said blackleg resistance locus.

28. The method according to paragraph 27, wherein said screening is done according to the Lem-08-syl AFLP Identification Protocol.

29. A method for detecting the presence or absence of Lem-08-syl in the DNA of *B. napus* or *B. juncea* tissue or seeds, comprising performing the Lem-08-syl AFLP Identification Protocol.

30. A kit for the detection of Lem-08-syl in *B. napus* or *B. juncea* DNA samples, wherein said kit comprises one or more PCR primer pairs, which are able to amplify a DNA marker linked to Lem-08-syl.

31. The kit according to paragraph 30, wherein said PCR primer pairs are selected from primer pairs E32/M50, P34/M48, P31/M59, E32/M48, E31/M61 and E36/M51.

32. The kit according to paragraph 31, wherein said primer pairs are able to amplify a DNA fragment of about 362 bp, 283 bp, 97 bp, 162 bp, 237 bp or 171 bp, respectively.

33. The kit according to any one of paragraphs 30 to 32, further comprising seeds or tissue, wherein DNA extracted from said seeds or tissue can be used as a positive or negative control.

34. An AFLP marker for *B. napus*, selected from the group consisting of: E32/M50-M362, E36/M51-M171.1, P34/M48-M283.

35. A method for monitoring the introgression of Lem-08-syl in *Brassica* oilseed plants or for AFLP analysis of *Brassica* oilseed plants, comprising the step of: using any one of AFLP markers E32/M50-M362, E36/M51-M171.1, P34/M48-M283, P31/M59-M97.1, E32/M48-M162.7 and E31/M61-M237.6.

36. The method of paragraph 35 wherein said *Brassica* oilseed plant is *Brassica napus*, comprising the step of using AFLP markers E32/M50-M362, E36/M51-M171.1, or P34/M48-M283.

37. A plant cell derived from the seeds deposited under deposit number PTA-5410, which plant cell after in vitro cultivation in the appropriate media provides a plant with a blackleg resistance gene on chromosome N08, which gene is derived from *B. rapa*.

38. A method for producing oilseed rape oil or an oilseed rape seed cake, comprising the step of crushing seed of the plant of any one of paragraphs 1 to 15.

39. A method to produce seed comprising a blackleg resistance gene on chromosome 8, which gene is derived from *B. rapa*, comprising the step of growing the plant of any one of paragraphs 1 to 15 in a field.

40. A method to produce a crop of oilseed rape, comprising a blackleg resistance gene on chromosome 8, which gene is derived from *B. rapa*, said method comprising the step of growing the plant of any one of paragraphs 1 to 15 in a field.

41. The method of any one of paragraphs 19, 20 or 24 to 28, which also comprises the step selected from the group consisting of: obtaining doubled haploid plants containing a blackleg resistance gene on chromosome 8, in vitro cultivation, cloning or asexual reproduction.

Other embodiments of this invention are specified in the enclosed claims.

DETAILED DESCRIPTION OF THE EMBODIMENTS

Figure 1:
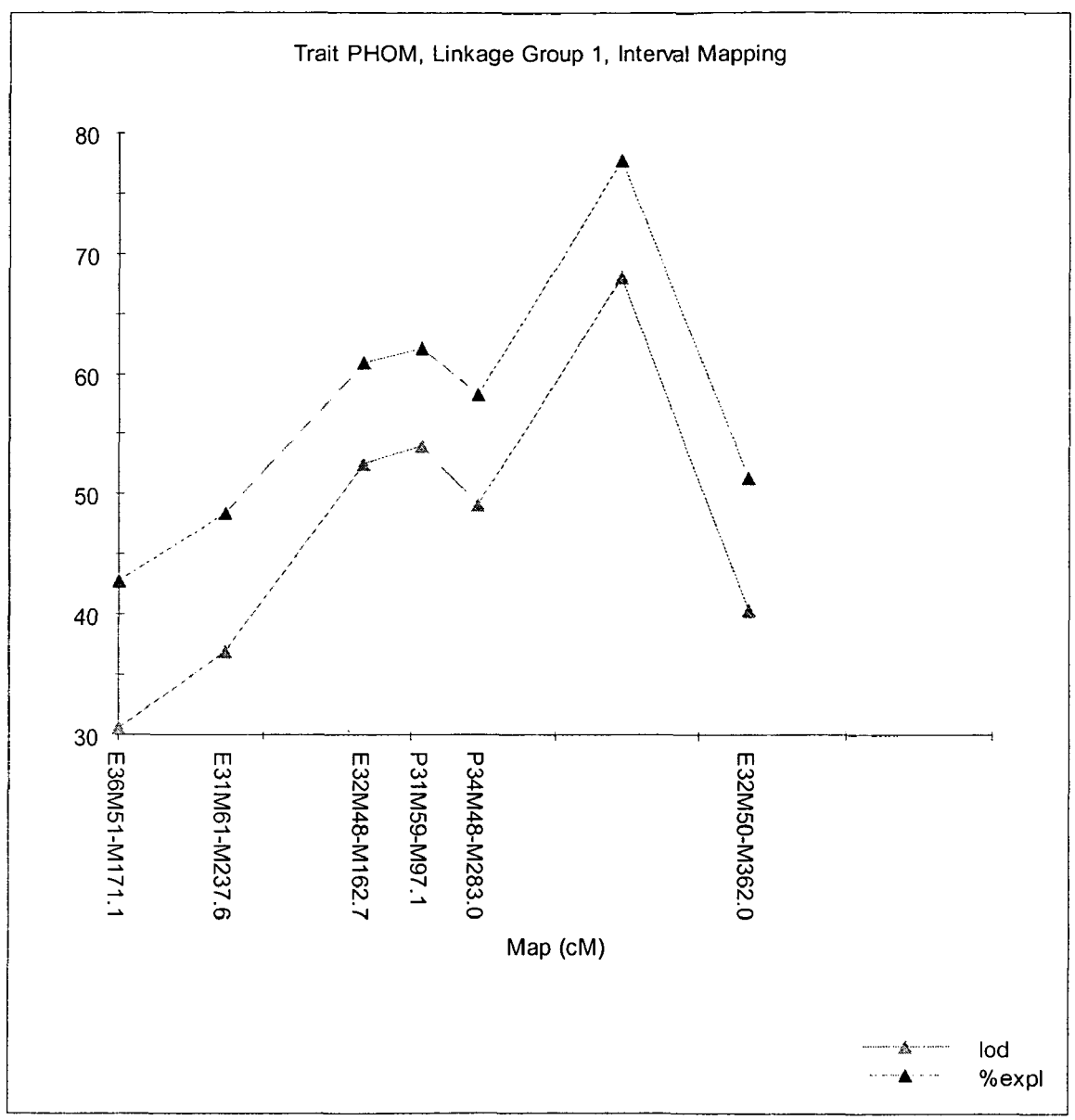
FIG. 1 shows interval mapping of blackleg resistance.

*B. napus* has 19 chromosome pairs, numbered herein N01 to N19, according to Sharpe et al. [(1995), *Genome* 38: 1112-1121] and Parkin et al. [(1995), *Genome* 38: 1122-1131]. N01 to N10 are A-genome chromosomes, while N11 to N19 are C-genome chromosomes. *B. rapa* (syn: *B. campestris*) has 10 chromosome pairs (A-genome), numbered herein R01 to R10, to correspond to *B. napus* N01 to N10. *B. juncea*, an amphidiploid species resulting from hybridization of diploid *B. nigra* and *B. rapa* ancestors, has 18 chromosome pairs, 10 originating from *B. rapa* (A-genome, herein numbered J01 to J10 to correspond to N01 to N10) and 8 from *B. nigra* (B genome).

In one embodiment of the invention *B. napus* plants or *B. juncea* plants are provided, which comprise on chromosome N08 or J08 (respectively) a fragment of a *B. rapa* chromosome 8 (R08), which carries a blackleg resistance gene, termed "Lem-08-syl" herein.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics, and is considered as a unit with regard to its suitability for being propagated unchanged.

"Lem-08-syl" as used herein refers to the blackleg resistance gene on chromosome 8 of *B. rapa*, which, when introgressed into a *Brassica napus* or *Brassica juncea* variety or breeding line susceptible to blackleg infection, confers blackleg resistance to such plant. Lem-08-syl is for example obtainable from seeds deposited at the ATCC (American Type Culture Collection, 10801 University Blvd, Manassas, Va. 20110-2209, USA) under accession number PTA-5410 on Aug. 22, 2003. Preferably, Lem-08-syl is the blackleg resistance gene derived from *B. rapa* and located on chromosome N08 of the seeds deposited under deposit number PTA-5410, preferably that gene associated with AFLP primers E32/M50-M362 and/or P34/M48-M283. In one embodiment of this invention, "Lem-08-syl" is that "blackleg resistance gene" which is associated with AFLP markers E32/M50-M362.0 and/or P34/M48-M283.0 at a distance of about 4.7 and/or about 5.7 cM, respectively, in seeds deposited at the ATCC under accession number PTA-5410.

When introgressed into a blackleg susceptible cultivar such as Kristina, Lem-08-syl enhances blackleg resistance from a score of about 1.0-2.0 to a score of about 6.0-9.0, when assessing blackleg resistance on a scale of 1.0 to 9.0, whereby 1.0 is the most susceptible and 9.0 is the most resistant phenotype. It is understood that environmental conditions, such as location, weather conditions and disease pressure, as well as individual perception of the person assessing disease symptoms, can have an effect on the scoring of blackleg resistance. Hence, variation in these factors in comparative tests should be minimized. Any other resistance ratings known in the art can be applied in accordance with this invention to compare the plants of the invention with control plants, e.g., the WA Blackleg resistance ratings set out in Khangura et al. (2003, Department of Agriculture, Western Australia, Farmnote No. 6/2003, ISSN 0726-934x).

The introgressed *B. rapa* fragment comprising Lem-08-syl is, in one embodiment, derived from wild *B. rapa* subspecies, preferably from subspecies *sylvestris*, but may also be derived from other *B. rapa* accessions, such as wild European or wild Asian accessions, as described in Song et al. [(1990), *TAG* 79: 497-506] or from cultivated *B. rapa* varieties. It is understood, that the size of the introgressed *B. rapa* fragment may vary, as long as the blackleg resistance locus is retained. Presence of Lem-08-syl can be tested by detecting molecular markers linked to Lem-08-syl or by testing whether blackleg resistance is increased in the offspring of a cross between a susceptible or not completely resistant *Brassica* plant with a plant comprising Lem-08-syl. Preferably, the *B. rapa* fragment does not comprise any undesirable additional loci, such as, but not limited to, loci affecting flowering time, vernalization requirement, freezing tolerance, etc.

"Blackleg" as used herein refers to the disease caused by the fungal pathogen *Leptosphaeria maculans* or *Phoma lingam* (anamorph). The definition encompasses both $Tox^o$ and $Tox^+$ isolates, irrespective of whether these may be found to belong to different species in later taxonomic studies [Rouxel et al. (1995), *Blackleg News N° 4*].

*L. maculans* isolates can be classified into different pathogenicity groups (PG), depending on their specific interactions with *B. napus* cultivars Westar, Galcier and Quinta [Mengistu et al. (1991), *Plant Disease* 75: 1279-1282]. PG4 isolates cause sporulating lesions on all three cultivars, while PG3 isolates cause a resistance reaction on cotyledons of Quinta, and PG2 isolates cause a resistance reaction on cotyledons of Quinta and Glacier. PG1 isolates are nonpathogenic on these hosts. PG2, PG3 and PG4 isolates are also referred to as 'highly aggressive' or 'highly virulent' or 'strongly pathogenic' isolates, while PG1 isolates are referred to as 'non-aggressive' or 'non-virulent' or 'weakly pathogenic' in the literature. Sometimes the highly aggressive group is also termed 'A' while the weakly aggressive group is termed 'NA' [Badawy and Hoppe (1989), *J Phytopathology* 127: 146-157]. More recently, the highly aggressive group is distinguished from the weakly aggressive group by its production of toxins ($Tox^+$ isolates vs $Tox^o$ isolates) [reviewed by Rouxel et al, *Blackleg News* N° 4, (1995)]. $Tox^o$ isolates have been found to cause necrosis of the pith, unaccompanied by external symptoms, and it has been suggested that the effect on yield loss caused by $Tox^o$ isolates has been underestimated [Johnson and Lewis (1994), *Plant Pathology* 43: 269-277]. $Tox^o$ isolates are further distinguished into three groups, NA1, NA2 and NA3 and it has been suggested that NA1 isolates are predominant in Europe and NA2 isolates are more important in Canada [Gall et al. (1995), *Mycol Res* 99: 221-229].

"Foreign", as used herein, when referring to a gene or a transgene in a certain plant genus, species or variety, refers to a gene which is not normally present in plants of that genus, species or variety, or which has been added to the genome of that plant by genetic transformation using methods known in the art, or an endogenous gene which has been modified by chemical, radiation-induced or other plant mutagenesis methods.

A "locus" as used herein is the position that a gene occupies on a chromosome. A "blackleg resistance locus" refers to the position on the chromosome where a "blackleg resistance gene" is located. This position can be identified by the location on the genetic map of a chromosome. Included in this definition is the fragment (or segment) of genomic DNA of the chromosome on which the blackleg resistance locus is located.

"Chromosome 8", as used herein when referring to the location of the resistance gene of this invention, particularly Lem-08-syl, is chromosome number 8 of the A genome according to the nomenclature of Sharpe et al. (1995, *Genome* 38: 1112-1121).

A "blackleg resistance gene" as used herein refers to a DNA sequence which confers, or is associated with, enhanced resistance of a plant, preferably a *B. napus* plant, to *L. maculans*, compared to a plant lacking the resistance gene(s) or having a non-functional (or inactivated) form of the gene(s). "Lem-08-syl" is that "blackleg resistance gene" which is associated with AFLP markers E32/M50-M362.0 and P34/M48-M283.0 at a distance of about 4.7 and about 5.7 cM, respectively, in seeds deposited at the ATCC under accession number PTA-5410. This resistance gene can be transferred to different varieties of *B. napus*, and even to different species of *Brassica* plants, e.g. *B. juncea*, e.g., using the molecular markers of this invention.

Blackleg resistance derived from *B. rapa* ssp *sylvestris* was found to segregate as a single dominant gene (Lem-08-syl). Using a qualitative blackleg resistance measure, Lem-08-syl mapped to chromosome N08, preferably to the distal end of chromosome N08, of the genetic map of *B. napus*. The position and effect of Lem-08-syl was confirmed by QTL mapping (Quantitative Trait Loci mapping), whereby the peak of the QTL identified corresponded to the position of Lem-08-syl on the genetic map and explained 77.8% of the variance for blackleg resistance (LOD (logarithm of the odds) score of 68.12), showing that Lem-08-syl has a highly significant effect on blackleg resistance.

"Enhanced resistance" of plants comprising a certain resistance gene refers to a reduction in damage caused by fungal infection compared to damage caused on control plants. Damage can be assessed as, for example, the number and size of leaf symptoms, frequency and severity of stem symptoms, lodging of plants due to stem infection, etc. In particular, the reduction in damage is manifested in a reduced yield loss when plants are grown under disease pressure in the field, compared to control plants. Such reduction in yield loss can, for example, be due to the fact that the infection, reproduction, spread or survival of the fungus is reduced or prevented in plants with enhanced resistance. Enhanced resistance may also refer to plants that are completely resistant, i.e., plants on which no disease symptoms are found or plants which get the highest resistance scores in available blackleg scoring or rating assays, e.g., Khangura et al. (2003, Department of Agriculture, Western Australia, Farmnote No. 6/2003, ISSN 0726-934x).

Enhanced resistance can also be assessed in bioassays carried out in controlled environments, such as growth chambers, but ideally are confirmed in field trials, as controlled environment assessments often do not reflect field conditions. This may be due to the fact that few, single spore isolates of the fungus are normally tested in bioassays, while in the field much larger variation in the pathogen population exists [see Crouch et al., supra].

An "allele" as used herein is one of a series of possible alternative forms of a gene. In a diploid species there are two alleles present at a given locus, although more than two alleles for the locus may exist in the population. If the two alleles at a corresponding locus of homologous chromosomes are the same, one refers to the locus being homozygous. For example double haploid (DH) plants, which are generated by chromosome doubling, are homozygous at all loci.

A (molecular) "marker" as used herein refers to a measurable, genetic characteristic with a fixed position in the genome, which is normally inherited in a Mendelian fashion, and which can be used for mapping of a trait of interest. The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet 32: 314-331; Tanksley et al. (1989), Bio/Technology 7: 257-263), RAPD [random amplified polymorphic DNA; Williams et al. (1990), NAR 18: 6531-6535], AFLP [Amplified Fragment Length Polymorphism; Vos et al. (1995) *NAR* 23: 4407-4414], SNPs or microsatellites [also termed SSR's; Tautz et al. (1989), NAR 17: 6463-6471]. Appropriate primers or probes are dictated by the mapping method used.

The term "AFLP®" (AFLP® is a registered trademark of KeyGene N.V., Wageningen, The Netherlands), "AFLP analysis" and "AFLP marker" is used according to standard terminology [Vos et al. (1995), *NAR* 23: 4407-4414; EP0534858]. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment. It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome. AFLP markers are generally dominant (homozygous and heterozygous individuals are not distinguishable), although some AFLP markers can be scored as co-dominant (distinguishing homozygous and heterozygous individuals, e.g., by band intensity).

A molecular marker is said to be "linked" to a gene or locus, if the marker and the gene or locus have a greater association in inheritance than would be expected from independent assortment, i.e. the marker and the locus co-segregate in a segregating population and are located on the same chromosome. "Linkage" refers to the genetic distance of the marker to the locus (or two loci or two markers to each other). The closer the linkage, the smaller the likelihood of a recombination event taking place, which separates the marker from the gene or locus. Genetic distance (map distance) is calculated from recombination frequencies and is expressed in centiMorgans (cM) [Kosambi (1944), *Ann. Eugenet.* 12: 172-175].

An AFLP marker can be linked to a gene or locus in "coupling phase" or in "repulsion phase'. For example, a dominant AFLP marker linked in coupling to a gene or locus is present in individuals with the gene or locus and absent in individuals without the gene or locus, while a dominant AFLP marker linked in repulsion phase to a gene or locus is absent in individuals with the gene or locus and present in individuals without the gene or locus. The AFLP markers of the present invention, which are linked to Lem-08-syl, are preferably linked in coupling to Lem-08-syl. Likewise, AFLP markers linked to other blackleg resistance genes or loci described herein, such as Lem-10-syl, are preferably linked in coupling to Lem-10-syl.

"*B. rapa* specific AFLP marker" as used herein is an AFLP marker, which is normally only present in diploid *B. rapa* plants, and not in allotetraploid *Brassica* species, preferably not in *B. napus* or in *B. juncea*. In one embodiment of this invention, a *B. rapa* specific AFLP marker is a marker present in *B. rapa* but not present in *B. napus*, preferably not present in any one of the following *B. napus* varieties: Surpass400, Tapidor, Doublol, Mohican, Columbus, Aglona, Apache, Falcon, Silex, Kana, Express, Apex, Bristol, Vivol, Polo (W), Orient, Mandarin, Sh7, Wuhac96.40006, Wuh5365, NAN93-1046, LE043-3, Yu-dal, Wuhan96.40005, Sh97.1020, Monty, Narendra, Drakkar, Kristina, Spok, Acrobat, Cyclone, or Stellar, particularly a marker present in *B. rapa* but not present in *B. napus* var. *Kristina*. For example, a *B. rapa* specific AFLP marker is not normally present in *B. napus* DNA or *B. juncea* DNA (unless introgressed into *B. napus* or *B. juncea* from a diploid *B. rapa*, especially a wild *B. rapa* accession). Thus, when carrying out an AFLP reaction with a *B. rapa* specific AFLP marker (using the specific AFLP primer combination of the marker) and using *B. napus* and *B. juncea* DNA (not comprising introgressed *B. rapa* segments), preferably DNA of the above listed varieties, as template DNA, there is no amplification product (no band) present on the AFLP gel at the expected marker position, whereas a band of the expected size is present when using *B. rapa* DNA as template. Examples of *B. rapa* specific AFLP markers linked to Lem-08-syl are E32/M50-M362.0, E36/M51-M171.1 or P34/M48-M283.0. A *B. rapa*-specific AFLP marker need not be mapped on any *B. rapa* chromosome in a genetic map, as long as it is found in *B. rapa* but not in *B. napus*, preferably not in the above listed *B. napus* plants, it is considered *B. rapa*-specific, as used herein. Also, additional *B. rapa* specific AFLP markers linked to Lem-08-syl can be generated by carrying out AFLP analysis as described in Example 1 and Example 2.

However, it is understood that AFLP markers can be converted into other types of molecular markers. When referring to a specific AFLP marker in the present invention, it is understood that the definition encompasses other types of molecular markers used to detect the genetic variation originally identified by the AFLP marker. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [(2001), *Mol Gen Genomics* 265 (2): 207-214], Negi et al. [(2000), *TAG* 101: 146-152], Barret et al. (1989), *TAG* 97: 828-833], Xu et al. [(2001), *Genome* 44(1): 63-70], Dussel et al. [(2002), *TAG* 105: 1190-1195] or Guo et al. [(2003), *TAG* 103: 1011-1017]. Dussel et al. [(2002), *TAG* 105: 1190-1195] converted AFLP markers linked to resistance into PCR-based sequence tagged site markers such as indel (insertion/deletion) markers and CAPS (cleaved amplified polymorphic sequence) markers.

The conversion of an AFLP marker into a STS marker generally involves the purification of the DNA fragment from the AFLP gel and the cloning and sequencing of the DNA fragment. Cloning and sequencing of AFLP fragments (bands) can be carried out using known methods [Guo et al. *TAG* 103: 1011-1017]. Based on the marker sequence (internal) locus specific PCR primers can be developed [Paran and Michelmore (1993), *TAG* 85: 985-993], which amplify fragments of different sizes or wherein the PCR product is cleaved with a restriction enzyme after amplification to reveal a polymorphism. As internal PCR primers often do not reveal polymorphisms related to the EcoRI, MseI or PstI (or other enzymes) restriction site differences, inverse PCR [Hartl and Ochmann (1996), In: Harwood A, editor, *Methods in molecular biology* vol 58: basic DNA and RNA protocols, Humana Press, Totowa N.J. pp 293-301] or PCR-walking [Negi et al. (2000), *TAG* 101: 146-152; Siebert et al, (1995), *NAR* 23:

1087-1088] may be used to identify flanking sequences, which can then be used to generate simple, locus specific PCR based markers. Primers can easily be designed using computer software programs such as provided by Sci-Ed (Scientific & Educational Software PO Box 72045, Durham, N.C. 27722-2045 USA). The polymorphism of the STS marker can be detected by gel electrophoresis, or can be detected using fluorometric assays, such as TaqMan® technology (Roche Diagnostics).

AFLP analysis with markers linked to Lem-08-syl is referred to hereinafter as the "Lem-08-syl AFLP Identification Protocol". In one embodiment of the invention, the Lem-08-syl AFLP Identification Protocol is performed with a B. rapa specific AFLP marker, such as, but not limited to, E32/M50-M362.0 or E36/M51-M171.1 and/or P34/M48-M283.0.

In one embodiment of the invention, the plants comprising a new blackleg resistance gene derived from chromosome R08 of B. rapa, preferably Lem-08-syl, as used herein, are B. juncea plants. In another embodiment of this invention, the plant comprising a new blackleg resistance gene derived from chromosome R08 of B. rapa, preferably Lem-08-syl, as used herein, is a B. napus plant that is selected from the group consisting of:

a B. napus plant that meets the canola quality standard set by the Canola Council of Canada (http://www.canola-council.org), a B. napus plant containing a transgene integrated into its genome, progeny of a B. napus plant containing said blackleg resistance gene, wherein said progeny results from crosses between B. napus plants containing said blackleg resistance gene and Surpass400 plants, a B. napus plant that contains a level of aliphatic glucosinolates in dry, defatted seed meal of less than 30 mmol/g, a B. napus plant the solid component of the seed contains less than 30 micromoles of any one or any mixture of 3-butehyl glucosinolate, 4-pentenyl glucosinolate, 3-hydroxy-3 butenyl glucosinolate, and 2-hydroxy-4-pentenyl glucosinolate per gram of air-dry, oil-free solid;

a B. napus plant that produces an oil (after crushing the seeds) containing less than 2% erucic acid (of the total fatty acids in the oil);

a B. napus spring oilseed rape plant, a B. napus winter oilseed rape plant, a B. napus plant that does not contain a blackleg resistance gene on chromosome N2, a B. napus plant that does not contain a blackleg resistance gene on chromosome N10;

a B. napus plants that does not contain a resistance gene mapped on chromosome 2 or a resistance gene mapped on chromosome 10, which resistance gene is derived from B. rapa ssp. Sylvestris, a B. napus plant comprising a transgene that can render plants male sterile, preferably a barnase gene;

progeny of a B. napus plant containing said blackleg resistance gene, wherein said progeny results from crosses between B. napus plants containing said blackleg resistance gene any one of the following oilseed rape varieties: a herbicide resistant B. napus variety, a B. napus variety with high oil content in its seeds, a B. napus variety with high oleic acid content (at least 70 percent, preferably at least 80 percent of total fatty acids) in its seeds, a B. napus variety with low linolenic acid content (less than 10 percent, preferably less than 5 percent of total fatty acids) in its seeds, Jet Neuf, Quantum, Maluka, Hyola43, Hyola60, Surpass400, Surpass402CL, Surpass603CL, Surpass501TT, a RoundupReady™ plant, a LibertyLink™ plant, a plant comprising a male sterility transgene, InVigor® 40, InVigor® 70, InVigor® 90, InVigor® 2573, InVigor® 2663, InVigor® 2733, InVigor® 5020, InVigor® 5030, or InVigor® 5070.

In one embodiment of the invention B. napus plants or B. juncea plants comprising at least one B. rapa specific molecular marker, which is linked to a blackleg resistance locus, are provided. In particular a B. napus or B. juncea plant comprising AFLP marker E32/M50-M362.0 and/or E36/M51-M171.1 and/or P34/M48-M283 linked to Lem-08-syl is provided.

In a further embodiment B. napus plants or B. juncea plants comprising at least one AFLP marker linked to Lem-08-syl are provided. For example, plants comprising one or more AFLP markers selected from P34/M48-M283.0, P31/M59-M97.1, E32/M48-M162.7, E31/M61-M237.6, E32/M50-M362.0 and/or E36/M51-M171.1 are provided. Additional AFLP markers linked to Lem-08-syl can be identified by known methods, such as for example, QTL mapping, Bulk Segregant Analysis [BSA; Michelmore et al. PNAS 88: 9828-9832] combined with AFLP analysis, as described in Examples 1 and 2. In order to identify more closely linked AFLP markers, more individual plants and more AFLP primer combinations are analyzed by AFLP analysis and the markers positioned on a genetic linkage map using known methods, and as described in the Examples. The linkage between the AFLP marker and the locus comprising Lem-08-syl is preferably close, i.e. preferably less than about 6 cM, more preferably less or equal to 5.7 cM, more preferably less than 5 cM, less or equal to 4.7 cM, and most preferably less than 4 cM. In one embodiment of the invention, Lem-08-syl is flanked by two dominant AFLP markers, such as E32/M50-M362.0 and P34/M48-M283.0, which are linked to Lem-08-syl in coupling at a distance of about 4.7 and about 5.7 cM, respectively, from Lem-08-syl.

AFLP markers linked to Lem-08-syl can be used for marker assisted selection (MAS) or map based cloning of Lem-08-syl. MAS involves screening plants for the presence or absence of linked markers. In particular plants are screened for the presence of markers flanking the linked gene or locus. Based on the presence/absence of the marker(s) plants are selected or discarded during the breeding program. MAS can significantly speed up breeding programs and introgression of a particular gene into another genetic background, and can also reduce problems with genotype x environment interactions. MAS is also useful in combining different blackleg resistance loci in one plant. The presence or absence of Lem-08-syl can be inferred from the presence or absence of AFLP markers linked to Lem-08-syl by e.g. using the Lem-08-syl AFLP identification protocol. For example, plants derived from seeds deposited at the ATCC under accession number PTA-5410 may be crossed to other B. napus plants and progeny from this cross are then screened for the presence of one or more AFLP markers linked to Lem-08-syl. AFLP analysis using, for example, closely linked AFLP marker(s), such as but not limited to E32/M50-M362.0 and/or P34/M48-M283.0, is carried out. Markers linked to Lem-10-syl can be used to combine Lem-08-syl and Lem-10-syl in one plant line, and to develop a new variety comprising two resistance loci derived from B. rapa.

Breeding procedures such as crossing, selfing, and backcrossing are well known in the art [see Allard R W (1960) Principles of Plant Breeding. John Wiley & Sons, New York, and Fehr W R (1987) Principles of Cultivar Development, Volume 1, Theory and Techniques, Collier Macmillan Publishers, London. ISBN 0-O₂-949920-8]. Lem-08-syl can be transferred into other breeding lines or varieties either by using traditional breeding methods alone or by using additionally MAS. In traditional breeding methods the blackleg resistance phenotype is assessed in the field or in controlled environment tests in order to select or discard plants comprising or lacking Lem-08-syl. Different crosses can be made to transfer Lem-08-syl into *B. napus* lines or varieties or into *B. juncea* lines or varieties. Lem-08-syl can be transferred to the A-genome of *B. juncea* by interspecific crosses between *B. napus* and *B. juncea* [Roy (1984), *Euphytica* 295-303]. The breeding program may involve crossing to generate an F1 (first filial generation), followed by several generations of selfing (generating F2, F3, etc.). The breeding program may also involve backcrossing (BC) steps, whereby the offspring are backcrossed to one of the parental lines (termed the recurrent parent). Breeders select for agronomically important traits, such as high yield, high oil content, oil profile, flowering time, plant height, disease resistance, resistance to pod shattering, etc., and develop thereby elite breeding lines (lines with good agronomic characteristics). In addition, plants are bred to comply with quality standards, such as 'canola' quality (less than 30 pmoles per gram glucosinolates in oil-free meal and less than 2% by weight erucic acid in the oil, see, e.g., U.S. Pat. No. 6,303,849B1 for canola quality *B. juncea*).

In another embodiment of the invention, the blackleg resistance gene derived from *B. rapa*, particularly from *B. rapa* chromosome 8, preferably Lem-08-syl, is transferred into other *Brassica* breeding lines or varieties by transformation of such lines or varieties with the Lem-08-syl gene, isolated from the plants of the invention, preferably from the plants deposited at the ATCC under accession number PTA-5410.

The "Lem-08-syl AFLP Identification Protocol" refers to the extraction of DNA from plant tissue such as leaf tissue or seeds and carrying out AFLP analysis for one or more of the linked AFLP markers. The Lem-08-syl identification protocol may be carried out on DNA obtained from individual plants or on DNA obtained from bulks (or pools). In one embodiment kits for detecting the presence of Lem-08-syl in *B. napus* or *B. juncea* DNA are provided. Such a kit comprises at least one PCR primer pair able to amplify a DNA marker linked to Lem-08-syl. The kit may comprise one or more of the following primer pairs: E32/M50, P34/M48, P31/M59, E32/M48, E31/M61 or E36/M51, able to amplify a DNA fragment of about 362 bp, 283 bp, 97 bp, 162 bp, 237 bp or 171 bp, respectively. In particular E32/M50 and/or P34/M48 are included in the kit. The kit may further comprise samples, which can be used as positive or negative controls and additional reagents for AFLP analysis, as described in Example 1. The samples may be tissue samples or DNA samples. As positive control for example seeds deposited at the ATCC under accession number PTA-5410 may be included or seeds derived therefrom. As negative controls seeds of cultivar Kristina or Stellar may be included.

In one embodiment of the invention hybrid *B. napus* plants and seeds comprising Lem-08-syl are provided. Hybrid seeds are generated by crossing two inbred parental lines, wherein one of the inbred parental lines comprises Lem-08-syl on chromosome N08. In order to produce pure hybrid seeds one of the parental lines is male sterile and is pollinated with pollen of the other line. By growing parental lines in rows and only harvesting the F1 seed of the male sterile parent, pure hybrid seeds are produced. To generate male sterile parental lines, the system as described in EP 0,344,029 or U.S. Pat. No. 6,509,516 may be used, wherein a gene encoding a phytotoxic protein (barnase) is expressed under the control of a tapetum specific promoter, such as TA29, ensuring selective destruction of tapetum cells. Transformation of plants with the chimeric gene pTA29:barnase results in plants in which pollen formation is completely prevented [Mariani et al. (1990), *Nature* 347: 737-741]. Cytochemical and histochemical analysis of anther development of *Brassica napus* plants comprising the chimeric pTA29-barnase gene is described by De Block and De Brouwer [(1993), *Planta* 189: 218-225]. To restore fertility in the progeny of a male-sterile plant the male-sterile plant (MS parent) is crossed with a transgenic plant (RF parent) carrying a fertility-restorer gene, which when expressed is capable of inhibiting or preventing the activity of the male-sterility gene [U.S. Pat. Nos. 5,689,041; 5,792,929; De Block and De Brouwer, supra]. The use of co-regulating genes in the production of male-sterile plants to increase the frequency of transformants having good agronomical performance is described in WO96/26283. Typically, when the sterility DNA encodes a barnase, the co-regulating DNA will encode a barstar, preferably an optimized barstar gene is used as described in published PCT patent application WO 98/10081. It is understood that different promoters may be used to drive barnase expression in order to render the plant male sterile. Likewise, barstar may be operably linked to different promoters, such as $^{35}$S from Cauliflower mosaic virus.

Male sterile plants can also be generated using other techniques, such as cytoplasmic male sterility/restorer systems [e.g. the Ogura system, published U.S. patent application 20020032916, U.S. Pat. No. 6,229,072, WO97/02737, U.S. Pat. No. 5,789,566 or the Polima system of U.S. Pat. No. 6,365,798, WO98/54340 or the Kosena system of WO95/09910, U.S. Pat. No. 5,644,066].

Either the MS parent or the RF parent, or both, may comprise Lem-08-syl on chromosome N08. This can be accomplished by either introgressing Lem-08-syl into an elite *B. napus* line and then transforming this line with pTA29-barnase or with pNOS-barstar using known methods. Alternatively Lem-08-syl may be introgressed directly into a transgenic MS or RF parent line, by crossing a plant comprising Lem-08-syl with the MS parent or RF-parent. The F1 hybrid seeds generated from the cross between the MS and RF parent will then contain Lem-08-syl.

The transgenic plants may additionally contain an endogenous or a transgene, which confers herbicide resistance, such as the bar or pat gene, which confers resistance to glufosinate ammonium (Liberty or Basta) [EP 0 242 236 and EP 0 242 246 incorporated by reference]; or any modified EPSPS gene, such as the 2mEPSPS gene from maize [EPO 508 909 and EP 0 507 698 incorporated by reference], which confers resistance to glyphosate (RoundupReady).

In a further embodiment, the invention provides methods of stacking (or pyramiding) blackleg resistance loci in a single plant line or variety, and in particular in hybrid seeds and hybrid plants. Although there is a maximum level of blackleg resistance which a plant can display (complete or nearly complete resistance), it is an advantage to stack blackleg resistance loci. Firstly, the different resistance loci may have different modes of action. This has the effect that the pathogen population is less likely to be able to overcome resistance or at least less likely to overcome resistance within a short period of time. Although a pathogen isolate may evolve (e.g., through mutation or genetic recombination) which is able to overcome one mode of action, it is less likely that a single isolate develops which is able to overcome several modes of action. In addition, different resistance loci may confer resistance at different stages of plant development. For example, one locus may confer resistance at the cotyledon stage, another locus to mature leaves and a further locus to stem infection. The durability of blackleg resistance in a plant comprising stacked resistance loci is enhanced, which means that resistance will not brake down (or brake down significantly later than it would if the plant only contained one major resistance locus) if the plant is grown on a large acreage in many locations. The invention provides methods and means to stack the blackleg resistance gene Lem-08-syl on chromosome N08 with additional blackleg resistance loci, such as, but not limited to Lem-10-syl (on chromosome N10, A-genome), Lem-07 (on chromosome N07, A-genome), Lem-14 (on chromosome N14, C-genome). In particular a plant comprising at least two blackleg resistance loci from wild *B. rapa* accessions, such as Lem-08-syl and Lem-10-syl, is provided.

In order to stack resistance loci in a single plant line or variety or in hybrid seeds and hybrid plants, the loci can be combined following general crossing and selection procedures.

Unless stated otherwise in the Examples, all recombinant DNA techniques are carried out according to standard protocols as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany. Standard procedures for AFLP analysis are described in Vos et al. (1995, NAR 23: 4407-4414) and in published EP patent application EP 534858.

It should be understood that the preceding is merely a detailed description of particular embodiments of this invention and that numerous changes to the disclosed embodiments can be made in accordance with the disclosure herein without departing from the spirit or scope of the invention. The preceding description, nor the following examples, are meant to limit the scope of the invention. Rather, the scope of the invention is to be determined only by the appended claims and their equivalents.

These are the sequences found in the enclosed sequence listing and referred to in the general description of the invention or in the examples:

| | |
|---|---|
| SEQ ID NO: 1: | MseI-adapter sequence 5'-3' |
| SEQ ID NO: 2: | MseI-adapter sequence 3'-5' |
| SEQ ID NO: 3: | EcoRI-adapter sequence 5'-3' |
| SEQ ID NO: 4: | EcoRI-adapter sequence 3'-5' |
| SEQ ID NO: 5: | PstI-adapter sequence 5'-3' |
| SEQ ID NO: 6: | PstI-adapter sequence 3'-5' |
| SEQ ID NO: 7: | AFLP primer E01 |
| SEQ ID NO: 8: | AFLP primer M01 |
| SEQ ID NO: 9: | AFLP primer M02 |

-continued

| | |
|---|---|
| SEQ ID NO: 10: | AFLP primer P01 |
| SEQ ID NO: 11: | AFLP primer E31 |
| SEQ ID NO: 12: | AFLP primer E32 |
| SEQ ID NO: 13: | AFLP primer E36 |
| SEQ ID NO: 14: | AFLP primer M48 |
| SEQ ID NO: 15: | AFLP primer M50 |
| SEQ ID NO: 16: | AFLP primer M51 |
| SEQ ID NO: 17: | AFLP primer M59 |
| SEQ ID NO: 18: | AFLP primer M61 |
| SEQ ID NO: 19: | AFLP primer P31 |
| SEQ ID NO: 20: | AFLP primer P34 |

EXAMPLES

Example 1

Mapping of Lem-08-syl by AFLP Analysis

Generation of BC3 and DH Mapping Populations

Kristina is a spring oilseed rape (SOSR) variety susceptible to blackleg infection. RFM292 is a synthetic *B. napus* line. RFM292 was generated by crossing a wild *B. rapa* ssp *sylvestris* accession from Sicily (#75) [Crouch et al. (1994)] with a wild *B. atlantica* accession from Tunisia (#25) [Mithen and Magrath (1992)], rescuing the embryos and doubling the chromosomes by colchicine treatment, as described in Crouch et al. (1994).

Kristina was crossed with RFM292. F1 plants derived from this cross were backcrossed to Kristina, generating a BC1 population, which was selfed to generate BC1S1 plants. Resistance of BC1S1 plants was tested in a field trial and resistant lines selected for further selfing, to generate BC1S3 plants. In order to select plants for selfing they were tested for resistance to various blackleg isolates (Canadian, Australian, British isolates). Resistant BC1S3 lines were then backcrossed again twice to Kristina to generate a BC2 and BC3 population. 300 BC3 plants were tested for blackleg resistance in growth chamber assays. Pools of resistant BC3 plants and pools of susceptible BC3 plants were analyzed by AFLP Bulk Segregant Analysis (BSA) [Michelmore et al. *PNAS* 88: 9828-9823] as described below, in order to identify AFLP markers linked to blackleg resistance. In addition, 300 BC3 plants were subjected to AFLP analysis in order to map blackleg resistance as described below.

Further, a double haploid (DH) population was derived from the F1 (BC2 individuals) of a cross between Kristina and BC1S3 through microspore culture [Mollers et al. (1994), *Euphytica* 75: 95-104]. The DH population was used to verify the multiple phenotyping, the mapping results obtained from the BC3 analysis and the linkage of AFLP markers to the blackleg resistance gene Lem-08-syl.

Amplified Fragment Length Polymorphism (AFLP) Analysis

DNA Extraction

DNA was extracted from parental lines, control lines, BC3 plants and DH plants using a modified CTAB protocol. Ten leaf discs (diameter 0.8 cm) per sample were frozen in liquid nitrogen, macerated with pestle and mortar and transferred to Eppendorf tubes. 1 ml CTAB buffer (100 ml=10 ml 1 M Tris-HCl pH7.5, 28 ml 5M NaCl, 4 ml 0.5M EDTA, 1 g CTAB, water) was added to each sample and Eppendorfs were incubated at 65° C. for 90 minutes and inverted several times during incubation. After brief centrifugation, 500 µl chloroform/isoamylalcohol (24/1) was added and samples homogenated for 5 minutes. The Eppendorf tubes were then centrifuged at 7,000 rpm for 10 minutes and the supernatant transferred to clean Eppendorfs. DNA was precipitated by adding 1 ml isopropanol and centrifugation at 13,000 rpm for 10 minutes. The pellet was washed with 500 µl wash-solution (76% EtOH, 0.2M NaOAc) for 20 minutes, followed by a second wash (76% EtOH, 0.01 M $NH_4Oac$) for 10 minutes. The pellets were air-dried and dissolved in 100 µl TE (1 M Tris-HCl pH8, 5M EDTA). (CTAB=hexadecyltrimethyl-ammoniumbromide).

AFLP Analysis

AFLP analysis was adapted from Vos et al. (1995). Genomic DNA was restricted with the restriction enzymes MseI and EcoRI or with MseI and PstI and adapters (Proligo®) were ligated to the restricted fragments (adapter sequences as described in Vos et al. (1995), EP 0534858 and U.S. Pat. No. 6,045,994].

```
Adapter sequences:
MseI-adapter:
5'GACGATGAGTCCTGAG 3'          (SEQ ID NO: 1)
3'TACTCAGGACTCAT 5'            (SEQ ID NO: 2)

EcoRI-adapter:
5'CTCGTAGACTGCGTACC 3'         (SEQ ID NO: 3)
3'CTGACGCATGGTTAA 5'           (SEQ ID NO: 4)

PstI-adapter:
5'CTCGTAGACTGCGTACATGCA 3'     (SEQ ID NO: 5)
3'CATCTGACGCATGT 5'            (SEQ ID NO: 6)
```

Restriction digest and adaptor ligation was carried out in a single reaction in microtiter plates by adding 10 µl restriction-mix (5 U EcoRI, 5 U MseI, 4 µl OPA-buffer, water until 10 µl volume) and 10 µl adapter ligation-mix (50 pMole MseI adapter, 5 pMole EcoRI adapter, 1 µl 10 mM ATP, 1 µl OPA-buffer, 5 U T4-ligase, water to a volume of 10 µl) to DNA samples (30 µl volume), followed by incubation at 37° C. for 4 hours. Samples were diluted 10-fold with TE0.1 (10 mM Tris.HCl pH 8, 0.1 mM EDTA).

AFLP primer sequences correspond to Vos et al. (1995), EP 0534858 and U.S. Pat. No. 6,045,994 (Proligo®). Pre-amplification with +1 primers (having one base selective extension) was carried out in microtiter plates (Biozyme) using a Hybaid Omnigene PCR cycler [Cycle 1: 94° C. for 30 seconds (denaturing), 65° C. for 30 seconds (annealing), 72° C. for 60 seconds (elongation); cycles 2-13: annealing temperature is lowered by 0.7° C. per cycle; cycles 14-36: 94° C. for 30 seconds, 56° C. for 30 second, 72° C. for 60 seconds]. Pre-amplification mix consisted of 5 µl of 10-fold diluted DNA template, 25 µl primer/dNTP mix (10×=750 ng µl of each primer, 20 µl 5 mM dNTPs, 200 µl water), 20 µl Taq-polymerase/buffer mix (10×=50 µl 10×PCR buffer, 2 µl Taq-polymerase (5 U/µl), 148 µl water) covered by 50 µl mineral oil. For selective restriction fragment amplification (using the pre-amplified DNA as template)+3 primers (having 3 bases selective extension) were used.

```
+1 primers:
5'-GAC TGC GTA CCA ATT C|A-3'      E01(SEQ ID NO: 7)

5'-GAT GAG TCC TGA GTA A|A-3'      M01(SEQ ID NO: 8)
```

```
5'-GAT GAG TCC TGA GTA A|C-3'      M02(SEQ ID NO: 9)

5'-GAC TGC GTA CAT GCA G|A-3'      P01(SEQ ID NO: 10)

+3 primers:
5'-GAC TGC GTA CCA ATT C|AA A-3'   E31(SEQ ID NO: 11)

5'-GAC TGC GTA CCA ATT C|AA C-3'   E32(SEQ ID NO: 12)

5'-GAC TGC GTA CCA ATT C|AC C-3'   E36(SEQ ID NO: 13)

5'-GAT GAG TCC TGA GTA A|CA C-3'   M48(SEQ ID NO: 14)

5'-GAT GAG TCC TGA GTA A|CA T-3'   M50(SEQ ID NO: 15)

5'-GAT GAG TCC TGA GTA A|CC A-3'   M51(SEQ ID NO: 16)

5'-GAT GAG TCC TGA GTA A|CT A-3'   M59(SEQ ID NO: 17)

5'-GAT GAG TCC TGA GTA A|CT G-3'   M61(SEQ ID NO: 18)

5'-GAC TGC GTA CAT GCA G|AA A-3'   P31(SEQ ID NO: 19)

5'-GAC TGC GTA CAT GCA G|AA T-3'   P34(SEQ ID NO: 20)
```

The EcoRI or PstI primer was labeled with γ33 P-ATP. The reaction mix consisted of 5 µl template DNA (10× diluted pre-amplification product), 5 µl primer/dNTP mix (10×=50 ng labeled primer, 300 ng unlabeled primer, 8 µl mM dNTPs, water to 50 µl), 10 µl Taq-polymerase/buffer mix (10×=20 µl 10×PCR-buffer, 0.8 µl Taq-polymerase, water to 100 µl) and 20 µl mineral oil. 10×PCR-buffer consists of 100 mM Tris pH8.3, 15 mM MgCl2, 500 mM KCl. PCR cycles were identical to those used for the pre-amplification.

PCR products were separated on 4.5% denaturing polyacrylamide gels (2.5 h at 110 W), together with a sequamark 10-bp DNA ladder. Dried gels were exposed overnight (Fujifilm, BAS-MS 2040 screens) and scanned on a Fuji BAS-2500 scanner. The digital gel images were analysed using AFLP-Quantar PRO software (KeyGene).

Polymorphic bands (markers) were scored and AFLP markers were named based on the specific +3 primer combination with which they were generated, followed by the approximate molecular weight of the polymorphic band (estimated by comparison to the 10-bp ladder). For example, E32/M50-M362.0 refers to a band of about 362 base pairs in size, generated by selective restriction fragment amplification with the primer pair E32 and M50. Monomorphic markers (i.e. a band of a certain size, present in all plants) were not scored.

Phenotyping of BC3 Plants in Growth Chamber Tests

300 BC3 plants were tested for blackleg resistance in growth chamber tests. A number of control lines, such as cultivar Kristina, Stellar, Surpass400 and line RFM292 were included in the tests (about 40-50 plants per line).

The single spore *L. maculans* (*Phoma lingam*) isolate Leroy1 was used in the disease resistance tests. Leroy1 is a Canadian isolate. The fungal isolate was grown on V8 agar plates (1 liter=800 ml water, 200 ml V8 juice, 0.75 g $CaCO_3$, 15 g Difco agar, 40 mg Rose Bengal and 100 mg/l streptomycin sulphate to prevent bacterial growth) for 1-2 weeks at 25° C. in the dark, followed by 1-2 days under UV light (14/10 hrs light/dark) at 20° C. Pycnidiospores were harvested by flooding plates with 5 ml sterile distilled water and losening spores with a sterile glass-rod. Spores were filtered through nylon mesh (45 µm), centrifuged at 3500 rpm for 10 minutes and resuspended in sterile distilled water. Spore concentrations were measured using a hemocytometer and adjusted to $10^7$ spores/ml using sterile distilled water. Spore suspensions were stored at −20° C.

Seeds of B. napus plants were surface sterilized and sown in standard soil in multipot trays and transferred after about 3 weeks to 10 cm diameter pots. Plants were grown in growth chambers for about 2.5 weeks at 18-20° C. (day), 14 h/10 h (light/dark), 70% relative humidity until three true leaves were emerged. Inoculations were carried out by wounding the petiole of the oldest leaf with a needle close to the stem (two wounds of about 0.5 cm) and by applying one small, superficial prick with the needle into the stem close to the leaf axis. 10 μl of spore suspension ($10^7$ spores/ml) was applied to the wounded stem. Humidity in the growth chamber was maintained at 100% rh for 3 days.

After nine weeks stem symptoms were assessed. Both external and internal symptoms were scored. External symptoms were scored by measuring the circumventing lesion (girdling) (A). Internal symptoms were scored by cutting through the stem base (horizontally) with secateurs and scoring the percentage of the stem diameter showing disease symptoms (B) and by measuring the length of the internal lesion (by cutting the stem along the vertical axis) (C). All stem scores were made on a scale of 0 (no symptoms) to 5 (most severe symptoms, e.g. complete girdling). An overall disease score was calculated as follows: Overall stem score=1×A+2×B+2×C. The overall stem score ranged from 0 to 25. Susceptible controls, such as Kristina, had consistently a score of 25.

Plants showed distinct phenotypes and could be divided in distinct classes based on the overall stem score using a cut off value of 12.5. 147 plants were resistant (R) and 140 susceptible (S) to blackleg. Thus, stem based resistance and susceptibility segregated in a 1:1 ratio ($Chi^2$=0.17) indicated a single, dominant blackleg resistance gene was segregating in the BC3 population, which was termed "Lem-08-syl".

Bulk Segregant Analysis (BSA)

In order to identify AFLP markers linked to Lem-08-syl, BSA was carried out according to Michelmore et al. [(1991), PNAS 88: 9828-9823]. The phenotypic data obtained for the 300 BC3 plants in the growth chamber test above was used to select the most resistant and most susceptible lines for BSA. Four pools of five resistant individuals and six pools of five susceptible individuals were generated. DNA pools were generated by pooling equal amounts of pre-amplificiation products. Then pools were tested by AFLP analysis using 47 (+3) AFLP primer combinations.

Polymorphic AFLP fragments (markers) present only in the resistant pools and absent in (most of) the susceptible pools were scored. Scoring was only done for AFLP markers linked to the resistance in coupling (i.e. from the donor parent). No scoring was done for markers linked to susceptibility (i.e. in repulsion, from the recurrent parent). 41 AFLP markers were found to be (partially) discriminating between resistant and susceptible pools. 12 of the best AFLP markers were selected (based on the quality of the pattern and on the best ability to discriminate between resistant and susceptible pools) to screen initially 43 individual plants of the above bulks of the BC3 population (20 resistant and 23 susceptible individuals) in order to analyze linkage of the markers.

Linkage analysis was carried out using the 12 AFLP markers and the phenotypic marker (Lem-08-syl) using JoinMap Version 3.0 [Van Ooijen and Vorrips, (2001), JoinMap Version 3.0, Software for the calculation of genetic linkage maps, Plant Research International, Wageningen, The Netherlands]. The pairwise recombination frequencies between markers within a linkage group were calculated using default parameters of JoinMap V3.0, using the Kosambi algorithm [Kosambi (1944), Ann. Eugenet. 12: 172-175]. The relative marker order and distance between markers was also calculated using JoinMap V3.0 default settings.

Linkage analysis grouped 4 dominant AFLP markers and Lem-08-syl on one linkage group. The other 7 AFLP markers were grouped together in a separate group, and were not considered further. The four linked AFLP markers, which were present in the pool of resistant plants and absent in the pool of susceptible plants were E32/M50-M362.0*, E32/M48-M162.7, E31/M61-M237.6 and E36/M51-M171.1*. Two of these markers (labeled by*) were B. rapa specific markers, meaning that at the corresponding position no band is found in cultivated B. napus, while the marker is present in the diploid species B. rapa. This indicated that lem-08-syl was introgressed from the wild B. rapa accession. These two markers were positioned on an in-house B. rapa map on chromosome R08. As R08 corresponds to N08 in B. napus, the B. napus linkage group was named N08 [in accordance with Sharpe et al. (1995), Genome 38: 1112-1121].

Lem-08-syl therefore mapped to the distal end of chromosome 8 (N08) on the B. napus map, as shown below:

| N08 Based on: | 43 BC3 plants | 259 BC3 plants |
|---|---|---|
| E32/M50-M362.0* | 0.0 | 0.0 |
| Lem-08-syl | 4.7 | 6.6 |
| E32/M48-M162.7 | 10.8 | 14.4 |
| E31/M61-M237.6 | 13.2 | 19.1 |
| E36/M51-M171.1* | 15.5 | 23.2 |

*B. rapa specific AFLP marker
Genetic distances between loci are given in centiMorgans (cM).

The B. rapa specific AFLP markers E32/M50-M362.0 and E36/M51-M171.1 flanked Lem-08-syl, confirming that Lem-08-syl is located on a DNA segment introgressed from B. rapa ssp sylvestris.

Example 2

Generation of More Closely Linked AFLP Markers

In order to generate AFLP markers, which are more closely linked to Lem-08-syl, addition pools of BC3 plants were subjected to BSA analysis (as described above). New resistant and susceptible pools were generated and screened using +3 PstI/MseI AFLP primer combinations. Two additional markers linked to Lem-08-syl were identified, P34/M48-M283.0 and P31/M59-M97.1. P34/M48-M283.0 is not yet mapped in B. rapa, but was found to be present in B. rapa and was found to be absent from B. napus, and hence provides another B. rapa-specific marker.

Example 3

Linkage Mapping Using 259 Individual BC3 Plants

AFLP analysis of 259 of the 300 BC3 plants was carried out using the 6 AFLP primer combinations identified above, namely E32/M50, P34/M48, P31/M59, E32/M48, E31/M61 and E36/M51. Using the phenotypic data obtained from growth chamber tests for the 300 BC3 plants (as described above) and these AFLP data, linkage analysis was carried out using JoinMap V3.0.

The following genetic map was generated:

| N08 | |
|---|---|
| E32/M47-M178.4 | 0.0 |
| E32/M50-M362.0 | 7.5 |
| Lem-08-syl | 12.2 |
| P34/M48-M283.0 | 17.9 |
| P31/M59-M97.1 | 19.3 |
| E32/M48-M162.7 | 21.4 |
| E31/M61-M237.6 | 26.0 |
| E36/M51-M171.1 | 29.3 |

The two mapped B. rapa specific markers flanked a region of about 21 cM, which was confirmed on an in-house B. rapa map.

QTL mapping (interval mapping) was also carried out using the same AFLP data and the overall blackleg score (quantitative score) for the 300 BC3 plants. The peak of the QTL identified corresponded to the position of Lem-08-syl on the genetic map, and explained 77.8% of the variance for blackleg resistance (LOD score of 68.12, LOD threshold of 3.0) (see FIG. 1).

In conclusion, 6 AFLP markers linked to Lem-08-syl were identified. The most closely linked AFLP markers were E32/M50-M362.0 and P34/M48-M283.0.

Example 4

Confirmation of Linked AFLP Markers in the DH Mapping Population

In order to confirm the finding that there is a perfect correlation between the presence (or absence) of AFLP markers E32/M50-M362.0 and P34/M48-M283.0 and the presence (or absence) of Lem-08-syl resistance, the DH lines 5 (described in Example 1) were analyzed for blackleg resistance in field trials in Canada and Australia in 2001.

The DH lines were also screened for the presence of AFLP markers E32/M50-M362.0 and P34/M48-M283.0. DNA was extracted from 2 leaf discs per DH line and AFLP analysis, as described above, was carried out using primer combinations E32/M50 and P34/M48. Presence of a band of about 362 bp or 283 bp for PC E32/M50 and PC P34/M48, respectively, was scored as a plus (+). As negative control DNA from B. napus cultivars Kristina and Stellar was used. Also, a BC1 S3 line (34B) known not to comprise Lem-08-syl was included as negative control. As positive control line BC1S3-45B, known to comprise Lem-08-syl, was included. Based on the AFLP analysis, a prediction was made, whether or not the plant line contained Lem-08-syl and was resistant to blackleg infection. The prediction was confirmed in the field trials below.

AFLP Analysis Results:

| Plant line | E32/M50-M362.0 | P34/M48-M283.0 | Predicted blackleg resistance[1] |
|---|---|---|---|
| Control: cv Kristina | − | − | S |
| Control: cv Stellar | − | − | S |
| Control: BC1S3 line 45B | + | + | R |
| Control: BC1S3 line 34B | − | − | S |
| DH line 77-2-1 | − | − | S |
| DH line 77-2-2 | − | − | S |
| DH line 77-2-5 | − | − | S |
| DH line 77-2-6 | − | − | S |
| DH line 77-2-8 | − | − | S |
| DH line 77-3-1 | − | − | S |
| DH line 77-3-2 | − | − | S |
| DH line 77-3-3 | − | − | S |
| DH line 77-3-4 | − | − | S |
| DH line 77-3-5 | − | − | S |
| DH line 77-3-6 | + | + | R |
| DH line 77-3-8 | − | − | S |
| DH line 77-3-9 | − | − | S |
| DH line 77-3-10 | − | − | S |
| DH line 77-3-12 | + | + | R |
| DH line 15-11-1 | − | − | S |
| DH line 15-11-7 | − | − | S |
| DH line 15-11-8 | − | − | S |
| DH line 15-11-9 | + | + | R |
| DH line 15-11-13 | + | + | R |
| DH line 15-11-15 | − | − | S |
| DH line 15-11-17 | − | − | S |
| DH line 15-11-23 | + | + | R |
| DH line 15-14-1 | − | − | S |
| DH line 15-14-2 | + | + | R |
| DH line 15-14-4 | − | − | S |
| DH line 15-14-6 | − | − | S |
| DH line 15-14-8 | + | + | R |
| DH line 15-14-10 | − | − | S |
| DH line 15-14-12 | − | − | S |
| DH line 15-14-13 | − | − | S |

R = resistant to blackleg,
S = susceptible to blackleg,
[1] = based on presence/absence of markers The DH lines contained the two flanking AFLP markers were predicted to contain Lem-08-syl, and were therefore predicted to be resistant to blackleg infection. In order to test blackleg resistance of the DH lines, field trials were carried out.

Field Trials in Canada

Seeds of the DH lines were sown in single rows and two repetitions in Canada. The mean blackleg score of the two repetitions was calculated and is given in the table below. Control lines, such as Kristina, Stellar, Westar, Quantum, Dunkeld and/or Oscar were included. Blackleg resistance was assessed per row at maturity on a scale of 1 to 9, adapted from NIAB.

Blackleg Disease Score:
1=majority of plants dead
2-3=significant proportion of plants dead or dying
4-6=majority of plants have canker at the base of the stem but little plant death
7-8=small amount of canker at base of stem and little or no plant death
9=no external stem canker symptoms and no plant death

| Plant line | Mean blackleg score (score 1-9) | Observed blackleg resistance of line | Predicted blackleg resistance [1] |
|---|---|---|---|
| Control: cv Kristina | 2.0 | S | S |
| Control: BC1S3 line 45B | 8.5 | R | R |
| Control: BC1S3 line 34B | 3.0 | S | S |

-continued

| Plant line | Mean blackleg score (score 1-9) | Observed blackleg resistance of line | Predicted blackleg resistance [1] |
|---|---|---|---|
| DH line 77-2-1 | 2.0 | S | S |
| DH line 77-2-2 | 1.0 | S | S |
| DH line 77-2-5 | 2.0 | S | S |
| DH line 77-2-6 | 1.25 | S | S |
| DH line 77-2-8 | 1.0 | S | S |
| DH line 77-3-1 | 2.0 | S | S |
| DH line 77-3-2 | 1.5 | S | S |
| DH line 77-3-3 | 1.0 | S | S |
| DH line 77-3-4 | 2.0 | S | S |
| DH line 77-3-5 | 1.0 | S | S |
| DH line 77-3-6 | 7.0 | R | R |
| DH line 77-3-8 | 1.0 | S | S |
| DH line 77-3-9 | 1.0 | S | S |
| DH line 77-3-10 | 1.5 | S | S |
| DH line 77-3-12 | 9.0 | R | R |
| DH line 15-11-1 | 1.0 | S | S |
| DH line 15-11-7 | 1.5 | S | S |
| DH line 15-11-8 | 2.0 | S | S |
| DH line 15-11-9 | 7.0 | R | R |
| DH line 15-11-13 | 6.0 | R | R |
| DH line 15-11-15 | 1.0 | S | S |
| DH line 15-11-17 | 2.0 | S | S |
| DH line 15-11-23 | 8.0 | R | R |
| DH line 15-14-1 | 1.0 | S | S |
| DH line 15-14-2 | 8.0 | R | R |
| DH line 15-14-4 | 2.0 | S | S |
| DH line 15-14-6 | 2.0 | S | S |
| DH line 15-14-8 | 7.0 | R | R |
| DH line 15-14-10 | 1.5 | S | S |
| DH line 15-14-12 | 2.0 | S | S |
| DH line 15-14-13 | 1.0 | S | S |

R = resistant to blackleg,
S = susceptible to blackleg,
[1] = based on presence/absence of markers The blackleg resistance phenotype predicted by the presence of the AFLP markers flanking Lem-08-syl, was confirmed in the Canadian field trial, as shown in the above table.

Field Trials in Australia

Seeds of a selection of DH lines and various control lines were sown at two locations in Australia. Both sites were seeded into the stubble of commercial canola crops, to provide a high level of disease pressure.

At both sites two replicates of single three meter rows were seeded. Blackleg infection was assessed twice at each location, once at flowering time, and once at maturity. Resistance was visually assessed on each row on a scale of 1 to 9. The mean of the two replicates was calculated.

Blackleg Disease Score:
1=majority of plants dead
2-3=significant proportion of plants dead or dying
4-6=majority of plants have canker at the base of the stem but little plant death
7-9=small amount of canker at base of stem and little or no plant death
9=no external stem canker symptoms and no plant death As shown in the table below, the DH lines which contained the linked AFLP markers and were predicted to be blackleg resistant, were also observed to be resistant to blackleg infection in the field at flowering time. One exception was DH line 77-3-6, which had statistically not significantly higher resistance than the mean, and was categorized as 'intermediate'.

| Line | Predicted blackleg resistance[1] | Mean blackleg score (1-9) at flowering, location 1 | Mean blackleg score (1-9) at flowering, location 2 | Observed resistance |
|---|---|---|---|---|
| Control: cv Kristina | S | 2.0* | 1.5* | S |
| Control: cv Stellar | S | 2.0* | 1.5* | S |
| Control: BC1S3 line 45B | R | 9.0*** | 8.5*** | R |
| Control: BC1S3 line 34B | S | 6.0 | 6.0 | I |
| DH line 77-2-1 | S | 6.5 | 4.5 | I |
| DH line 77-2-2 | S | 1.0* | 1.0* | S |
| DH line 77-3-2 | S | 6.0 | 5.0 | I |
| DH line 77-3-3 | S | 5.5 | 5.5 | I |
| DH line 77-3-5 | S | 5.5 | 4.0 | I |
| DH line 77-3-6 | R | 6.0 | 6.5 | I |
| DH line 77-3-12 | R | 9.0*** | 8.5*** | R |
| DH line 15-11-8 | S | 7.0 | 4.0 | I |
| DH line 15-11-9 | R | 8.0*** | 8.0*** | R |
| DH line 15-11-13 | R | 8.5*** | 8.5*** | R |
| DH line 15-11-15 | S | 2.5* | 1.5* | S |
| DH line 15-11-23 | R | 8.0*** | 7.0 | R |
| DH line 15-14-2 | R | 7.5*** | 8.0*** | R |
| DH line 15-14-8 | R | 7.5*** | 8.0*** | R |
| DH line 15-14-10 | S | 5.5 | 2.5* | S |
| DH line 15-14-12 | S | 7.0 | 6.0 | I |

S = susceptible,
R = resistant,
I = Intermediate,
[1] = based on presence/absence of linked AFLP markers
* = significantly less resistant than the mean
*** = significantly more resistant than the mean As shown in the table below, all lines which contained the linked AFLP markers and were predicted to be resistant to blackleg, were also resistant to blackleg infection in the field at maturity (again with the exception of line 77-3-6), although resistance levels at maturity (i.e. towards the end of the growing season) were lower than during flowering (meaning of asterisks is as above).

| Line | Predicted blackleg resistance[1] | Mean blackleg score (1-9) at maturity, location 1 | Mean blackleg score (1-9) at maturity, location 2 | Observed resistance |
|---|---|---|---|---|
| Control: cv Kristina | S | 1.0* | 1.0* | S |
| Control: cv Stellar | S | 1.0* | 1.0* | S |
| Control: BC1S3 line 45B | R | 6.5*** | 7.0*** | R |
| Control: BC1S3 line 34B | S | 4.0 | 4.0 | I |
| DH line 77-2-1 | S | 3.0 | 1.0* | S |
| DH line 77-2-2 | S | 1.0* | 1.0* | S |
| DH line 77-3-2 | S | 4.0 | 1.5 | I |
| DH line 77-3-3 | S | 4.0 | 2.5 | I |
| DH line 77-3-5 | S | 4.0 | 2.5 | I |
| DH line 77-3-6 | R | 4.0 | 5.0 | I |
| DH line 77-3-12 | R | 6.5*** | 7.5*** | R |
| DH line 15-11-8 | S | 4.0 | 2.5 | I |
| DH line 15-11-9 | R | 6.0*** | 6.0*** | R |
| DH line 15-11-13 | R | 6.5*** | 5.5 | R |
| DH line 15-11-15 | S | 1.0* | 1.0* | S |
| DH line 15-11-23 | R | 5.0 | 7.0*** | R |
| DH line 15-14-2 | R | 4.5 | 6.0*** | R |

-continued

| Line | Predicted blackleg resistance[1] | Mean blackleg score (1-9) at maturity, location 1 | Mean blackleg score (1-9) at maturity, location 2 | Observed resistance |
|---|---|---|---|---|
| DH line 15-14-8 | R | 7.0*** | 7.5*** | R |
| DH line 15-14-10 | S | 2.5* | 1.5 | S |
| DH line 15-14-12 | S | 4.0 | 3.5 | I |

In conclusion, the field trial data show that whenever the two AFLP markers flanking Lem-08-syl were present in the DNA, the plant was resistant to blackleg infection. The data thus confirm that the AFLP markers are linked to Lem-08-syl, and that they can be used to predict the plants' phenotype.

Seeds of DH line 77-3-12, comprising Lem-08-syl and linked AFLP markers, including *B. rapa* specific markers, in their genome, have been deposited at the American Type Culture Collection (ATCC, 10801 University Blvd, Manassas, Va. 20110-2209, USA) on Aug. 22, 2003 under accession number PTA-5410 by Bayer BioScience N.V. (the viability of the seeds was confirmed on Aug. 29, 2003). The deposit was made under the terms of the Budapest Treaty, and all restrictions to the availability of the deposited seeds will be irrevocably removed upon the issuance of a patent.

Example 5

"Lem-08-syl AFLP Identification Protocol" Shows the Absence of Lem-08-syl in Commercially Available *B. napus* Cultivars AFLP analysis (as described in Example 1) with markers linked to Lem-08-syl is referred to hereinafter as "Lem-08-syl AFLP Identification Protocol". In one embodiment of the invention, the Lem-08-syl AFLP Identification Protocol is performed with a *B. rapa* specific AFLP marker, such as, but not limited to, E32/M50-M362.0 or E36/M51-M171.1 and/or linked *B. napus* markers, such as P34/M48-M283.0.

To confirm the absence of Lem-08-syl in a range of available *B. napus* cultivars, the Lem-08-syl AFLP Identification Protocol was carried out (as described in Example 1) with primer combination (PC) E32/M50, PC E36/M51 and PC P34/M48.

The results of this protocol with pooled plant groupings were:

| | Marker | | |
|---|---|---|---|
| Sample | E32/M50-M362.0 | P34/M48-M283.0 | E36M51-M171.1 |
| RFM292 | + | + | + |
| Surpass400 | − | − | ND |
| POOL1 | − | − | − |
| POOL2 | − | − | − |
| POOL3 | − | − | − |
| POOL4 | − | − | − |
| POOL5 | − | − | − |
| POOL6 | − | − | − |
| POOL7 | − | − | − |
| POOL8 | − | − | − |
| POOL9 | − | − | − |
| POOL10 | − | − | − |
| POOL11 | − | − | − |

Legend:
Plus symbol (+) = fragment (band) of expected size present
Minus symbol (−) = no fragment (band) of expected size present
ND: not done
POOL1: Tapidor + Doublol + Mohican
POOL2: Columbus + Aglona + Apache
POOL3: Falcon + Silex + Kana
POOL4: Express + Apex + Bristol
POOL5: Vivol + Polo (W) + Orient
POOL6: Mandarin + Sh7 + Wuhac96.40006
POOL7: Wuh5365 + NAN93-1046 + LE043-3
POOL8: Yu-dal + Wuhan96.40005 + Sh97.1020
POOL9: Monty + Narendra + Drakkar
POOL10: Kristina + Spok
POOL11: Acrobat + Cyclone + Stellar Also, the absence of Lem-08-syl from other plant varieties is confirmed in a further AFLP analysis on the following varieties, using AFLP markers E32/M50-M362.0, P34/M48-M283, and E36/M51-M171.1: Surpass400, Hyola60, Hyola50, Apex, Excel, Maluka, Quantum. The positive control varieties in this analysis (including the above DH lines containing Lem-08-syl) show the presence of this resistance gene, as expected.

The above results show that commercial winter oilseed rape (WOSR) and spring oilseed rape (SOSR) cultivars, such as Surpass400, Hyola 60, Hyola 50, etc. do not contain the *B. rapa* specific AFLP markers E32/M50-M362.0 and E36/M51-M171.1, confirming that the *B. rapa* specific DNA fragment on chromosome 8, comprising Lem-08-syl, is absent from these cultivars.

Example 6

Mapping of Surpass400 Blackleg Resistance Loci

In order to map resistance loci present in Surpass400, a DH population was generated from a cross between a Canadian *B. napus* breeding line susceptible to blackleg infection and Surpass400 (commercial blackleg resistant cultivar of Pacific Seeds (Advanta)). The blackleg resistance in Surpass400 apparently originates from a cross between *B. rapa* ssp *sylvestris* and *B. oleracea* ssp. *alboglabra* [Li et al. (2001, supra)].

Resistance of the DH population was assessed in a field trial in Australia in 2002. AFLP analysis was carried out, to map blackleg resistance.

Three resistance loci could be mapped by QTL analysis:
    one major locus on chromosome N10 (A genome), herein referred to as Lem-10-syl
    one locus on chromosome N07 (A genome), herein referred to as Lem-07
    one locus on chromosome N14 (C genome), herein referred to as Lem-14

No resistance locus was found on chromosome N08. These data confirmed that Lem-08-syl is not present in Surpass400, although Surpass400 apparently also comprises blackleg resistance derived from wild *B. rapa* ssp *sylvestris* according to published information.

Plants with the resistance allele from parent Surpass400 at all 3 loci had a blackleg resistance score of 7-8 (on a scale of 1-9 as described above), and were thus resistant. Plants with the allele of the Canadian parent at all three loci had blackleg resistance scores of 3-4, and were thus susceptible.

It is likely that the blackleg resistance locus Lem-10-syl is derived from *B. rapa* ssp *sylvestris* (this would confirm the data of Rimmer et al.), while Lem-07 and Lem-14 are more likely derived from *B. napus*. Interestingly, no resistance locus was found on chromosome $NO_2$, although Yu et al. [*Plant, Animal & Microbe Genomes* Jan. 12-16, 2002, Poster 460] described the presence of a blackleg resistance locus derived from *B. rapa* on chromosome $NO_2$.

Example 7

Pyramiding of Lem-08-syl with Other Blackleg Resistance Loci

In order to generate a plant with strong and durable blackleg resistance, different resistance loci and resistance alleles were combined in a single plant (referred to as stacking or pyramiding of resistance). In this example, Lem-08-syl was combined with the resistance loci present in Surpass400, i.e. with Lem-10-syl, Lem-07 and Lem-14.

(a) Development of a Population that Contains Both Surpass400 Resistance and Lem-08-syl Resistance Several plants of Surpass 400 were hand emasculated and crossed with pollen from 4-5 plants from an F2 population 99-AN13. The 99-AN13 population was a segregating population that contains Lem-08-syl.

(b) Further Development of the Population

A small number of F1 plants were grown under high disease pressure in 2001. Two plants showing a resistant phenotype were selfed and selected. Further F2 and F3 plants have been selfed and single plant selections taken. Only plants showing a resistance phenotype have been selected.

In order to determine, whether the observed field resistance is due to the combined presence of both Lem-08-syl and one or more Surpass400 resistance loci, plants are screened with molecular markers linked to the different resistance loci, i.e. for example with markers linked to Lem-08-syl and markers linked to Lem-10-syl. Single plants comprising the desired combination of resistance loci are selected, while other plants are discarded.

Example 8

Hybrid Seed Production Methods

Hybrid *B. napus* seeds, comprising stacked blackleg resistance, are developed in different ways.

Scheme 1: Resistance Loci are Stacked in the Hybrid Seed

A male sterile (MS) female parent is developed, which comprises the barnase gene under the tapetum specific promoter pTA29 integrated in its genome, and which further comprises Lem-08-syl on chromosome N08. To develop this female parent, either a plant comprising Lem-08-syl is transformed with a chimeric gene comprising pTA29 operably linked to the barnase gene, or a male sterile, transgenic plant comprising pTA29 operably linked to the barnase gene is crossed with a plant comprising Lem-08-syl.

A male parent (RF) is developed, which comprises pTA29-barstar in its genome, as well as Lem-10-syl and/or other blackleg resistance loci.

To develop hybrid seeds, the MS parent is crossed with the RF parent, and the hybrid seeds are harvested from the female parent. Plants grown from these seeds are fully fertile, and comprise in their genome Lem-08-syl, and/or other resistance loci.

Scheme 2: Resistance Loci are Stacked in the Female Parent (MS)

A male sterile (MS) female parent is developed, which comprising the barnase gene under the tapetum specific promoter pTA29 integrated in its genome, and which further comprises several blackleg resistance loci in its genome, such as Lem-08-syl on chromosome N08, Lem-10-syl on chromosome 10 and/or other loci. To develop this female parent, either a plant comprising several blackleg resistance loci is transformed with a chimeric gene comprising pTA29 operably linked to the barnase gene, or a male sterile, transgenic plant comprising pTA29 operably linked to the barnase gene is crossed with a plant comprising several blackleg resistance loci in its genome. A male parent (RF) is developed, which comprises pTA29-barstar in its genome.

To develop hybrid seeds, the MS parent is crossed with the RF parent, and the hybrid seeds are harvested from the female parent. Plants grown from these seeds are fully fertile, and comprise in their genome Lem-08-syl, together with Lem-10-syl or other resistance loci.

Also, two further schemes are developed, such schemes are: 1) a scheme identical to the above scheme 1, except that the Lem-08-syl resistance gene is present in the RF plants, and 2) a scheme identical to scheme 2 above, except that the Lem-08-syl resistance gene is present in the RF plants.

All schemes are used to develop pure hybrids, having several blackleg resistance loci in their genome.

Similarly, hybrid seeds comprising Lem-08-syl alone can be developed.

Example 9

Transfer of Lem-08-syl into Other *Brassica* Elite Lines

Lem-08-syl is transferred into other elite breeding lines by the following method. A plant containing Lem-08-syl (donor plant), such as plants derived from the seeds deposited at the ATCC under accession number PTA-5410, is crossed with an elite *B. napus* line (elite parent/recurrent parent) or variety lacking Lem-08-syl. The following introgression scheme is used (Lem-08-syl is abbreviated to N08):

| | |
|---|---|
| Initial cross: | N08/N08 (donor plant) × wt/wt (elite parent) |
| F1 plant: | N08/wt |
| BC1 cross: | N08/wt × wt/wt (recurrent parent) |
| BC1 plants: | 50% N08/wt and 50% wt/wt |
| | The 50% N08/wt are selected using AFLP markers linked to Lem-08-syl |
| BC2 cross: | N08/wt (BC1 plant) × wt/wt (recurrent parent) |
| BC2 plants: | 50% N08/wt and 50% wt/wt |
| | The 50% N08/wt are selected using AFLP markers linked to Lem-08-syl |
| Backcrossing is repeated until BC6 | |
| BC6 plants: | 50% N08/wt and 50% wt/wt |
| | The 50% N08/wt are selected using AFLP markers linked to Lem-08-syl |
| BC6 S1 cross: | N08/wt × N08/wt |
| BC6 S1 plants: | 25% N08/N08 and 50% N08/wt and 25% wt/wt |
| | Plants containing N08 are selected using AFLP markers linked to Lem-08-syl |

Progeny test seed from individual BC6 S1 plants are tested for segregation of Lem-08-syl in order to select BC6 S1 plants, which are homozygeous for Lem-08-syl (N08/N08). These plants are then used for seed production.

In the above introgression scheme, backcross material is tested in each generation for the presence of AFLP markers linked to Lem-08-syl and lines are selected which contain Lem-08-syl. Instead of testing for the presence of Lem-08-syl using linked AFLP markers, plants can be tested in field trials for blackleg resistance, and plants with high resistance can be selected. However, this is only feasible if the elite line into which Lem-08-syl is to be introgressed does not already contain high levels of blackleg resistance. For example, if the elite line was Surpass400, which has very high blackleg resistance, marker assisted selection (marker assisted breeding) for Lem-08-syl needs to be carried out, as it would be extremely difficult to select material comprising the desired combination of resistance loci in the field. However, if the elite parent is a line, which is susceptible, or at least not as resistant as lines comprising Lem-08-syl, MAS (molecular assisted selection) in the above scheme can be replaced by selection in the field under high blackleg disease pressure.

The invention claimed is:

1. A cultivated *Brassica napus* plant, comprising on chromosome 8 a *Leptosphaeria maculans* resistance gene derived from *Brassica rapa*, wherein said *Brassica napus* plant is obtainable from seed as deposited under ATCC accession number PTA-5410 and wherein said resistance gene is associated with AFLP markers E32/M50-M362 and P34/M48-M283 on chromosome 8 in said seed.

2. The plant of claim 1, that produces an oil, after crushing the seeds, containing less than 2% erucic acid of the total fatty acids in the oil.

3. The plant of claim 1, wherein the solid component of the seed contains less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid.

4. The plant of claim 1, wherein said plant additionally contains an endogenous gene or a transgene which confers herbicide resistance.

5. The plant of claim 4, wherein said gene is the bar or pat gene, which confer resistance to glufosinate ammonium.

6. The plant of claim 4, wherein said gene is a modified EPSPS gene which confers resistance to glyphosate.

7. The plant of claim 1, wherein said plant is rendered male sterile by the expression of a first transgene.

8. The plant of claim 7, wherein said first transgene is a barnase gene.

9. The plant of claim 1, which was generated using cytoplasmic male sterility factors.

10. The plant of claim 1 which is a hybrid plant.

11. The plant of claim 1, wherein said *Leptosphaeria maculans* resistance gene is associated with at least one AFLP marker selected from the group consisting of: P34/M48-M283.0, E32/M50-M362.0, and E36/M51-M171.1.

12. The plant of claim 11, wherein said *Leptosphaeria maculans* resistance gene is flanked by AFLP marker E32/M50-M362.0 and AFLP marker P34/M48-M283.0.

13. The plant of claim 7, in which fertility is restored by the expression of a second transgene capable of inhibiting or preventing activity of said first transgene.

14. The plant of claim 13, wherein said first transgene is a barnase gene and said second transgene is a barstar gene.

15. The plant of claim 9, in which fertility is restored by the presence of cytoplasmic restorer factors.

16. The plant of claim 1 derived from the seeds deposited at the ATCC under accession number PTA-5410.

17. The plant according to claim 1, further comprising in its genome at least one additional blackleg resistance gene located on a different chromosome.

18. The plant of claim 17, wherein said additional resistance gene is located on chromosome N10, N14 and/or N 7, or where said additional resistance gene is from any one of the following B. napus cultivars: Jet Neuf, Quantum, Maluka, Hyola60, or Surpass 400.

19. The plant of claim 8, wherein said barnase gene is under control of a tapetum specific promoter in its genome.

20. Seeds of the plant of claim 1, comprising said Leptosphaeria maculans resistance gene.

21. Seeds deposited at the ATCC under accession number PTA-5410.

* * * * *